(12) United States Patent
Tsuchimoto et al.

(10) Patent No.: US 11,006,839 B2
(45) Date of Patent: May 18, 2021

(54) BIOMETRIC INFORMATION SENSOR

(71) Applicant: Murata Manufacturing Co., Ltd., Nagaokakyo (JP)

(72) Inventors: Hirofumi Tsuchimoto, Nagaokakyo (JP); Kengo Saito, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 15/431,866

(22) Filed: Feb. 14, 2017

(65) Prior Publication Data

US 2017/0150891 A1 Jun. 1, 2017

Related U.S. Application Data

(63) Continuation of application No. PCT/JP2015/071391, filed on Jul. 28, 2015.

(30) Foreign Application Priority Data

Aug. 15, 2014 (JP) .............................. JP2014-165459

(51) Int. Cl.
*A61B 5/02* (2006.01)
*A61B 5/024* (2006.01)
(Continued)

(52) U.S. Cl.
CPC .............. *A61B 5/02* (2013.01); *A61B 5/0205* (2013.01); *A61B 5/0245* (2013.01);
(Continued)

(58) Field of Classification Search
CPC ........ A61B 5/11; A61B 5/0205; A61B 5/0408; A61M 5/00
(Continued)

(56) References Cited

U.S. PATENT DOCUMENTS

2002/0151795 A1* 10/2002 Palti .................... A61B 8/06
600/454
2009/0005675 A1* 1/2009 Grunwald ............ A61B 5/0452
600/424
(Continued)

FOREIGN PATENT DOCUMENTS

JP 2006-518235 A 8/2006
JP 2010-508128 A 3/2010
(Continued)

OTHER PUBLICATIONS

Offcial Communication issued in corresponding International Application PCT/JP2015/071391, dated Oct. 20, 2015.

*Primary Examiner* — Jon Eric C Morales
(74) *Attorney, Agent, or Firm* — Keating & Bennett, LLP

(57) ABSTRACT

A biometric information sensor includes a flexible substrate, an adhesive, a heartbeat signal detector, an electrocardiographic signal detector, a pulse wave detector, and a signal processor. The signal processor calculates an electrocardiographic peak estimated value resulting from estimating the wave of an electrocardiographic signal detected by the electrocardiographic signal detector from a heartbeat signal detected by the heartbeat signal detector based on the heartbeat signal and the electrocardiographic signal. The signal processor estimates a pulse wave transmit time based
(Continued)

on the calculated electrocardiographic peak estimated value a photoplethysmographic signal detected by the pulse wave detector.

20 Claims, 12 Drawing Sheets

(51) Int. Cl.
*A61B 5/0205* (2006.01)
*A61B 5/0245* (2006.01)
*A61B 5/259* (2021.01)
*A61B 5/352* (2021.01)
*A61B 5/0456* (2006.01)
*A61B 5/0408* (2006.01)
*A61B 5/00* (2006.01)
*A61B 5/021* (2006.01)

(52) U.S. Cl.
CPC .......... *A61B 5/02416* (2013.01); *A61B 5/259* (2021.01); *A61B 5/352* (2021.01); *A61B 5/0002* (2013.01); *A61B 5/02125* (2013.01)

(58) Field of Classification Search
USPC ................ 600/484, 500, 301, 383, 384, 509
See application file for complete search history.

(56) References Cited

U.S. PATENT DOCUMENTS

| | | | |
|---|---|---|---|
| 2009/0008459 A1 | 1/2009 | Mainguet | |
| 2010/0179438 A1 | 7/2010 | Heneghan et al. | |
| 2010/0286607 A1* | 11/2010 | Saltzstein | A61B 5/02055 604/93.01 |
| 2011/0257536 A1* | 10/2011 | Ser | A61B 5/0816 600/484 |
| 2013/0267859 A1 | 10/2013 | Okuda et al. | |
| 2015/0038808 A1* | 2/2015 | Shimuta | A61B 5/0245 600/301 |
| 2015/0161342 A1* | 6/2015 | Takakura | G06F 19/3418 705/2 |
| 2016/0106320 A1* | 4/2016 | Shimuta | A61B 5/7246 600/301 |
| 2016/0151000 A1* | 6/2016 | Shimuta | A61B 5/7207 600/484 |
| 2018/0020931 A1* | 1/2018 | Shusterman | A61B 5/02055 600/483 |

FOREIGN PATENT DOCUMENTS

| | | |
|---|---|---|
| JP | 2012-101027 A | 5/2012 |
| JP | 2012-150696 A | 8/2012 |

* cited by examiner

BIOMETRIC INFORMATION SENSOR

CROSS REFERENCE TO RELATED APPLICATIONS

This application claims the benefit of priority to Japanese Patent Application No. 2014-165459 filed on Aug. 15, 2014 and is a Continuation Application of PCT Application No. PCT/JP2015/071391 filed on Jul. 28, 2015. The entire contents of each application are hereby incorporated herein by reference.

BACKGROUND OF THE INVENTION

1. Field of the Invention

The present invention relates to a biometric information sensor that measures biometric information of a person subjected to measurement (hereinafter referred to as an "object").

2. Description of the Related Art

Sensors that measure various types of biometric information including an electrocardiographic (ECG) signal and a pulse wave signal are generally known (for example, see Japanese Unexamined Patent Application Publication No. 2010-508128, Japanese Unexamined Patent Application Publication No. 2012-150696 and Japanese Unexamined Patent Application Publication No. 2006-518235. Japanese Unexamined Patent Application Publication No. 2010-508128 describes a system for measuring the heart rate of an object using a radio frequency signal reflected from the object. Japanese Unexamined Patent Application Publication No. 2012-150696 describes a biometrics card for obtaining electrocardiographic information such as an electrocardiographic waveform or a heart rate based on a potential difference obtained by bringing a right hand finger and a left hand finger into contact with first and second input electrodes, respectively. Japanese Unexamined Patent Application Publication No. 2006-518235 describes a chip card for measuring the pulse of an object by receiving light diffused inside the object's finger.

A pulse wave transit time is known as biometric information. This pulse wave transit time indicates a time difference from the R wave of an electrocardiographic signal to the minimum value of a pulse wave signal. In contrast, the sensors described in Japanese Unexamined Patent Application Publication No. 2010-508128, Japanese Unexamined Patent Application Publication No. 2012-150696 and Japanese Unexamined Patent Application Publication No. 2006-518235 calculate the heartbeats, electrocardiogram, pulses, and the like using various signals detected from the object, but these sensors do not calculate a pulse wave transit time. To calculate a pulse wave transit time, it is necessary to measure an electrocardiographic signal and a pulse wave signal at the same time. To do so, the object needs to be attached with electrodes for measuring an electrocardiographic signal, and a light-emitting element and a light-receiving element for detecting a pulse wave signal at the same time, and this puts the object under restraint and lowers convenience.

SUMMARY OF THE INVENTION

In view of the above-mentioned circumstances, preferred embodiments of the present invention provide biometric information sensors capable of calculating a pulse wave transit time while enhancing convenience.

A biometric information sensor according to a preferred embodiment of the present invention includes a heartbeat signal detector that detects a heartbeat signal of an object; and a signal processor that processes the heartbeat signal. The signal processor is connectable to an electrocardiographic signal detector that detects an electrocardiographic signal of the object and a pulse wave detector that detects a pulse wave signal of the object. The signal processor includes an electrocardiographic peak estimator that calculates an electrocardiographic peak estimated value by estimating an R wave of the electrocardiographic signal from the heartbeat signal based on the heartbeat signal detected by the heartbeat signal detector and the electrocardiographic signal detected by the electrocardiographic signal detector; and a pulse wave transmit time estimator that estimates a pulse wave transmit time from the R wave of the electrocardiographic signal to a minimum value of the pulse wave signal based on the electrocardiographic peak estimated value calculated by the electrocardiographic peak estimator and the pulse wave signal detected by the pulse wave detector.

According to a preferred embodiment of the present invention, the biometric information sensor includes the heartbeat signal detector and the signal processor. The signal processor is connectable to the electrocardiographic signal detector and the pulse wave detector. Therefore, the heartbeat signal, the electrocardiographic signal, and the pulse wave signal, which are the biometric information of the object, are able to be measured at the same time by the biometric information sensor.

The signal processor includes the electrocardiographic peak estimator, which estimates the R wave of the electrocardiographic signal from the heartbeat signal. Accordingly, the electrocardiographic peak is able to be indirectly estimated from the heartbeat signal based on the relationship between the electrocardiographic signal and the heartbeat signal. As a result, once the relationship between the electrocardiographic signal and the heartbeat signal is obtained, the electrocardiographic peak estimated value is able to be calculated by the heartbeat signal detector, without using the electrocardiographic signal detector.

The signal processor includes the pulse wave transmit time estimator, which estimates the pulse wave transmit time based on the electrocardiographic peak estimated value and the pulse wave signal. As a result, because the heartbeat signal detector is able to be used when calculating the pulse wave transmit time, the object is less constrained to enhance convenience, compared with the case of using the electrocardiographic signal detector. Also, the pulse wave transmit time is able to be easily estimated.

According to a preferred embodiment of the present invention, the heartbeat signal detector and the signal processor are provided on the flexible substrate, and an adhesive capable of being attached to a body surface of the object is provided on the flexible substrate.

According to a preferred embodiment of the present invention, using the flexible substrate and the adhesive, the heartbeat signal detector and the signal processor are able to be attached to the body surface of the object. Accordingly, because the biometric information sensor is able to be attached to the body surface near the heart of the object, the accuracy of detecting the heartbeat signal is able to be enhanced.

According to a preferred embodiment of the present invention, the electrocardiographic signal detector and the pulse wave detector are provided on the flexible substrate.

According to a preferred embodiment of the present invention, using the flexible substrate and the adhesive, the heartbeat signal detector, the signal processor, and the electrocardiographic signal detector are able to be attached to the body surface of the object. Accordingly, the heartbeat signal and the electrocardiographic signal are able to be detected at the same time using the heartbeat signal detector and the electrocardiographic signal detector, which are attached to the body surface of the object. As a result, the electrocardiographic peak estimated value is able to be calculated by the electrocardiographic peak estimator.

Since the pulse wave detector is provided on the flexible substrate, the pulse wave signal of the object is able to be easily detected while having the biometric information sensor attached to the body surface of the object.

According to the present invention, the heartbeat signal detector and the signal processor are provided in a card casing.

According to a preferred embodiment of the present invention, the heartbeat signal detector and the signal processor are provided in the card casing. Accordingly, a card biometric information sensor that is small and highly portable is able to easily detect the heartbeat signal of the object.

According to a preferred embodiment of the present invention, the electrocardiographic signal detector is provided in the card casing.

According to a preferred embodiment of the present invention, the heartbeat signal detector, the signal processor, and the electrocardiographic signal detector are provided in the card casing. Accordingly, the heartbeat signal and the electrocardiographic signal are able to be detected at the same time using the heartbeat signal detector and the electrocardiographic signal detector provided in the card casing, which enables calculation of the electrocardiographic peak estimated value by using the electrocardiographic peak estimator.

According to a preferred embodiment of the present invention, the signal processor is wired to the pulse wave detector.

According to a preferred embodiment of the present invention, the signal processor is wired to the pulse wave detector. Accordingly, the signal processor is able to measure both the heartbeat signal from the heartbeat signal detector and the pulse wave signal from the pulse wave detector without having a time delay between the two signals. Therefore, the pulse wave transmit time is able to be estimated based on the heartbeat signal and the pulse wave signal.

According to a preferred embodiment of the present invention, a pulse wave sensor includes the pulse wave detector and a transmitter that transmits the pulse wave signal to the signal processor, and the pulse wave sensor is wirelessly connected to the signal processor through a receiver that is connected to the signal processor and that receives the pulse wave signal and the transmitter.

According to a preferred embodiment of the present invention, the pulse wave sensor is wirelessly connected to the signal processor. Accordingly, compared with the case where the pulse wave sensor is wired to the signal processor, there is no wiring at the time of measurement, and convenience is enhanced.

According to a preferred embodiment of the present invention, a reference signal output that outputs a reference signal is connected to the signal processor. The receiver receives a response signal based on the reference signal from the pulse wave sensor. The signal processor corrects a signal delay relative to the pulse wave sensor based on the response signal.

According to a preferred embodiment of the present invention, because the reference signal output is connected to the signal processor, the signal processor is able to correct a signal delay relative to the pulse wave sensor based on a response signal in accordance with the reference signal. Accordingly, even when a signal transmission delay occurs between the pulse wave sensor and the signal processor, which are wirelessly connected to each other, the signal processor is able to estimate the pulse wave transmit time by taking the signal delay into consideration. As a result, the accuracy of estimating the pulse wave transmit time is enhanced.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
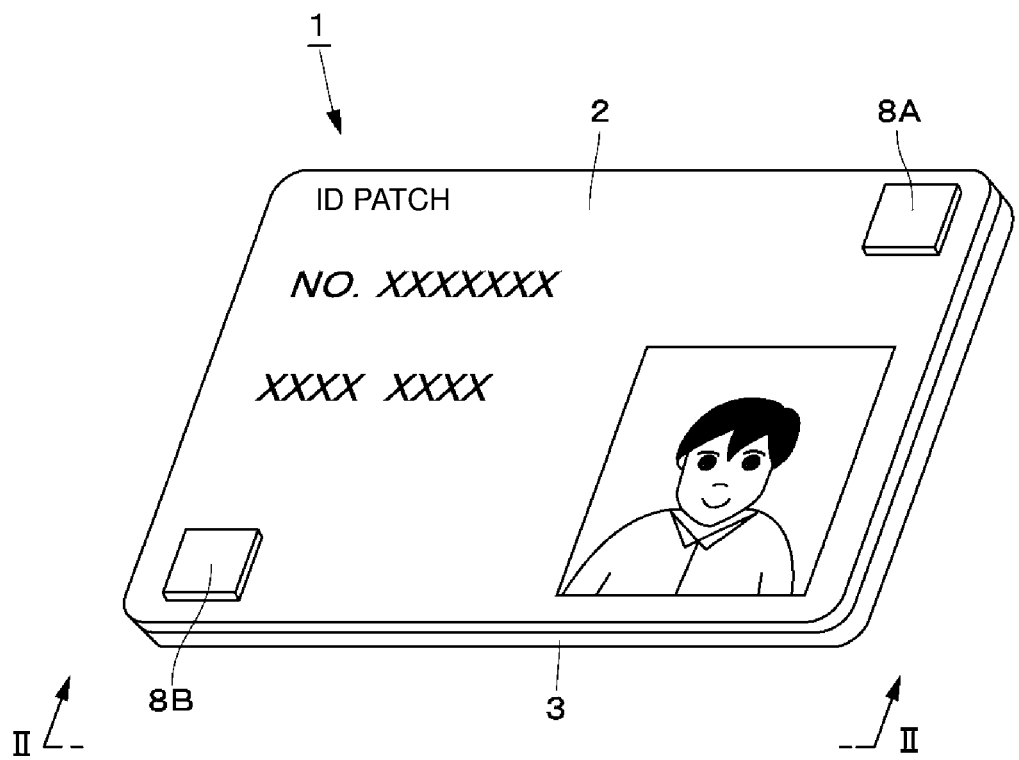
FIG. 1 is a perspective view illustrating a biometric information sensor according to a first preferred embodiment of the present invention.

Hereinafter, biometric information sensors according to preferred embodiments of the present invention will be described in detail with reference to the drawings.

At first, FIGS. 1 to 9 illustrate a first preferred embodiment of the present invention. A biometric information sensor 1 according to the first preferred embodiment includes a flexible substrate 2, an adhesive 3, a heartbeat signal detector 4, an electrocardiographic signal detector 7, a pulse wave detector 10, a signal processor 14, and the like.

The flexible substrate 2 preferably has, for example, a deformable planar shape and includes a resin material having an insulating property. The heartbeat signal detector 4, the electrocardiographic signal detector 7, the pulse wave detector 10, the signal processor 14, a battery 16, and the like are mounted on the flexible substrate 2. A back surface (bottom surface) of the flexible substrate 2 is a surface that faces the body surface of an object O. Therefore, the later-described adhesive 3 is provided on the back surface of the flexible substrate 2. In contrast, a front surface (top surface) of the flexible substrate 2 is a mounting surface on which detection electrodes 8A and 8B of the electrocardiographic signal detector 7, which will be described later, are mounted. In this case, a sealing resin layer 2A made of an insulating resin material such as epoxy resin is provided on the front surface of the flexible substrate 2, and the detection electrodes 8A and 8B are mounted on the front surface of the flexible substrate 2.

Figure 2:
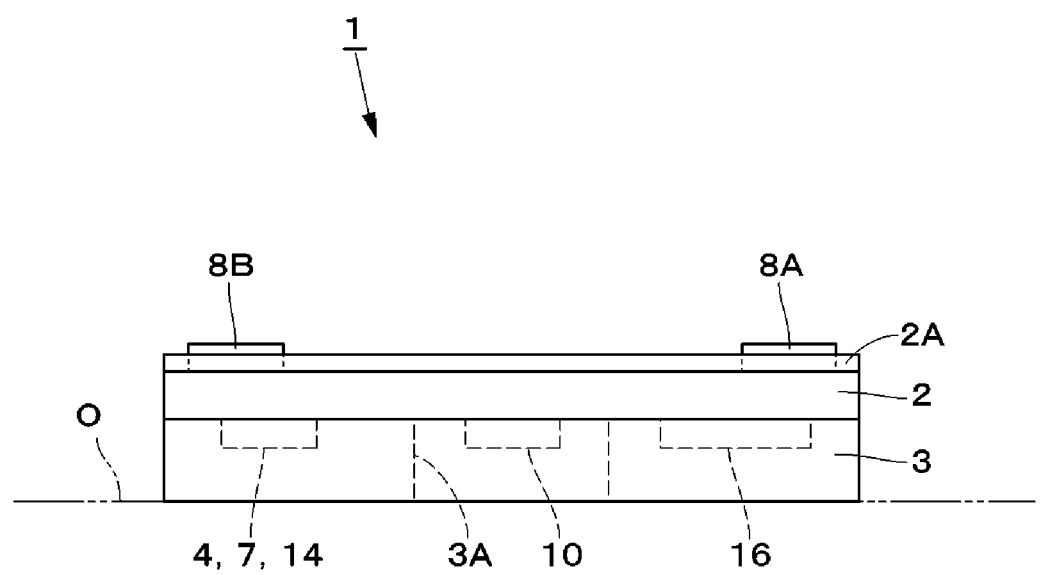
FIG. 2 is a bottom view illustrating the biometric information sensor, taken along reference arrow II-II illustrated in FIG. 1.
Figure 3:
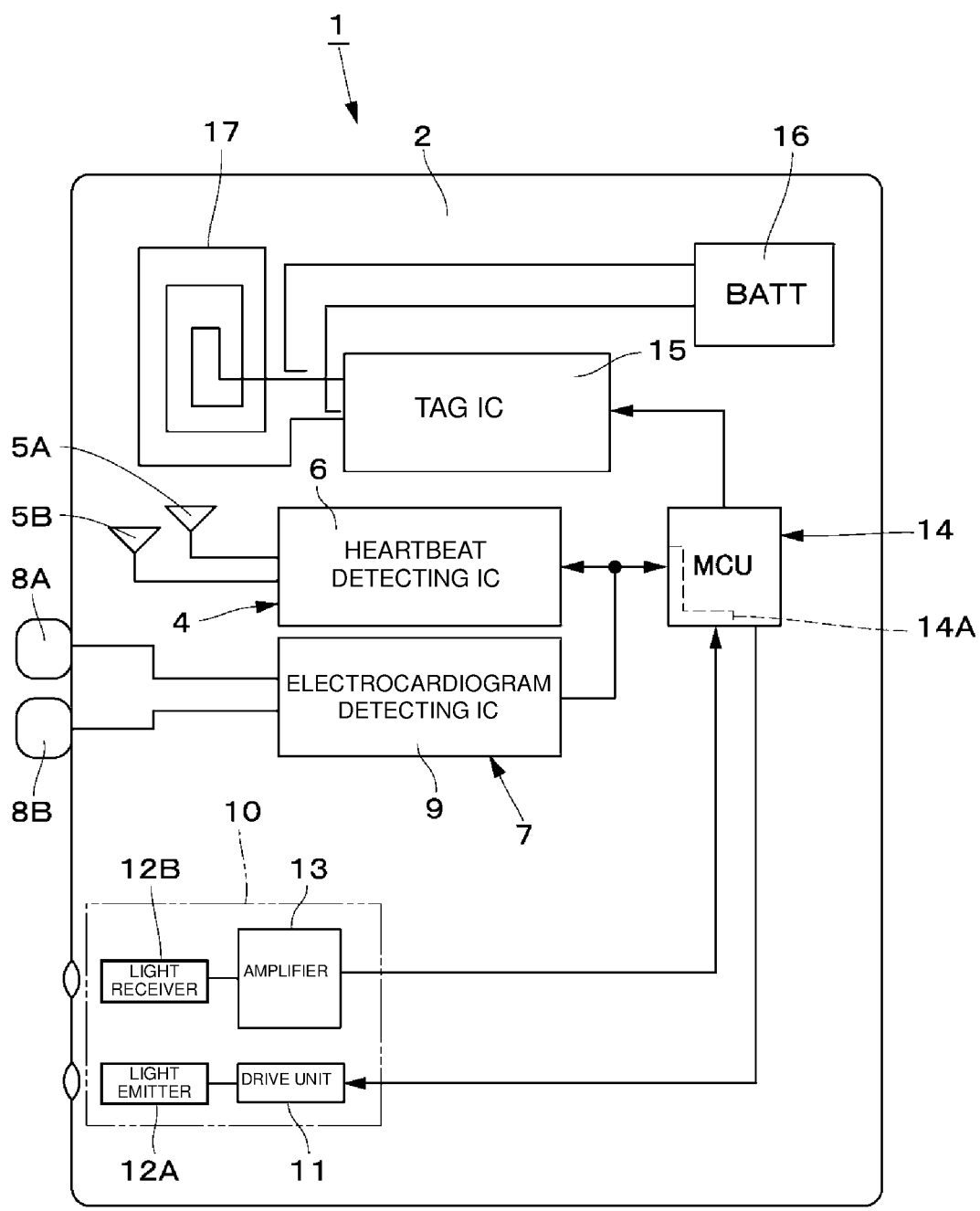
FIG. 3 is a schematic diagram illustrating the internal configuration of a biometric information sensor according to the first preferred embodiment of the present invention.

The adhesive 3 is provided on the back surface of the flexible substrate 2, and is, for example, a seal that is able to be adhered to the body surface of the object O for a long period of time. As illustrated in FIG. 2, a light transmission portion 3A that allows light to pass through between the pulse wave detector 10 and the body surface of the object O is provided at or substantially at a center of the adhesive 3. The light transmission portion 3A preferably includes a transparent material such as transparent resin. Although the light transmission portion 3A made of a transparent material is provided in the adhesive 3, the overall adhesive 3 may be made or include a transparent material, or the adhesive 3 may be provided with a through hole through which light passes.

The heartbeat signal detector 4 is provided on the flexible substrate 2 and includes a transmitting antenna 5A, a receiving antenna 5B, a heartbeat detecting IC chip 6, and the like. The heartbeat signal detector 4 detects a heartbeat signal HBR of the object O.

The transmitting antenna 5A is connected to the heartbeat detecting IC chip 6 and includes various antennas such as a patch antenna and a slot antenna. The transmitting antenna 5A outputs a transmission signal with a certain frequency, generated by the heartbeat detecting IC chip 6, toward a portion near the heart of the object O.

At this time, the transmission signal enters the body of the object O and is reflected by the heart of the object O.

Like the transmitting antenna 5A, the receiving antenna 5B is also connected to the heartbeat detecting IC chip 6 and includes various antennas such as a patch antenna and a slot antenna. The receiving antenna 5B receives, as a reception signal, a signal which is the transmission signal reflected by the object O. At this time, since the reception signal includes reflected waves that have been reflected by the heart of the object O, the intensity of the reception signal changes in accordance with the beating of the heart. Therefore, the reception signal is a signal obtained by adding the Doppler frequency based on the heartbeats of the object O to the frequency of the transmission signal. Although the heartbeat signal detector 4 separately includes the transmitting antenna 5A and the receiving antenna 5B, a transmission and receiving antenna that commonly performs transmission and reception may be used.

The heartbeat detecting IC chip 6 is mounted on the flexible substrate 2 using a solder or the like. The heartbeat detecting IC chip 6 is driven by power supplied from the battery 16 and is connected to the transmitting antenna 5A, the receiving antenna 5B, and the later-described signal processor 14.

Figure 4:
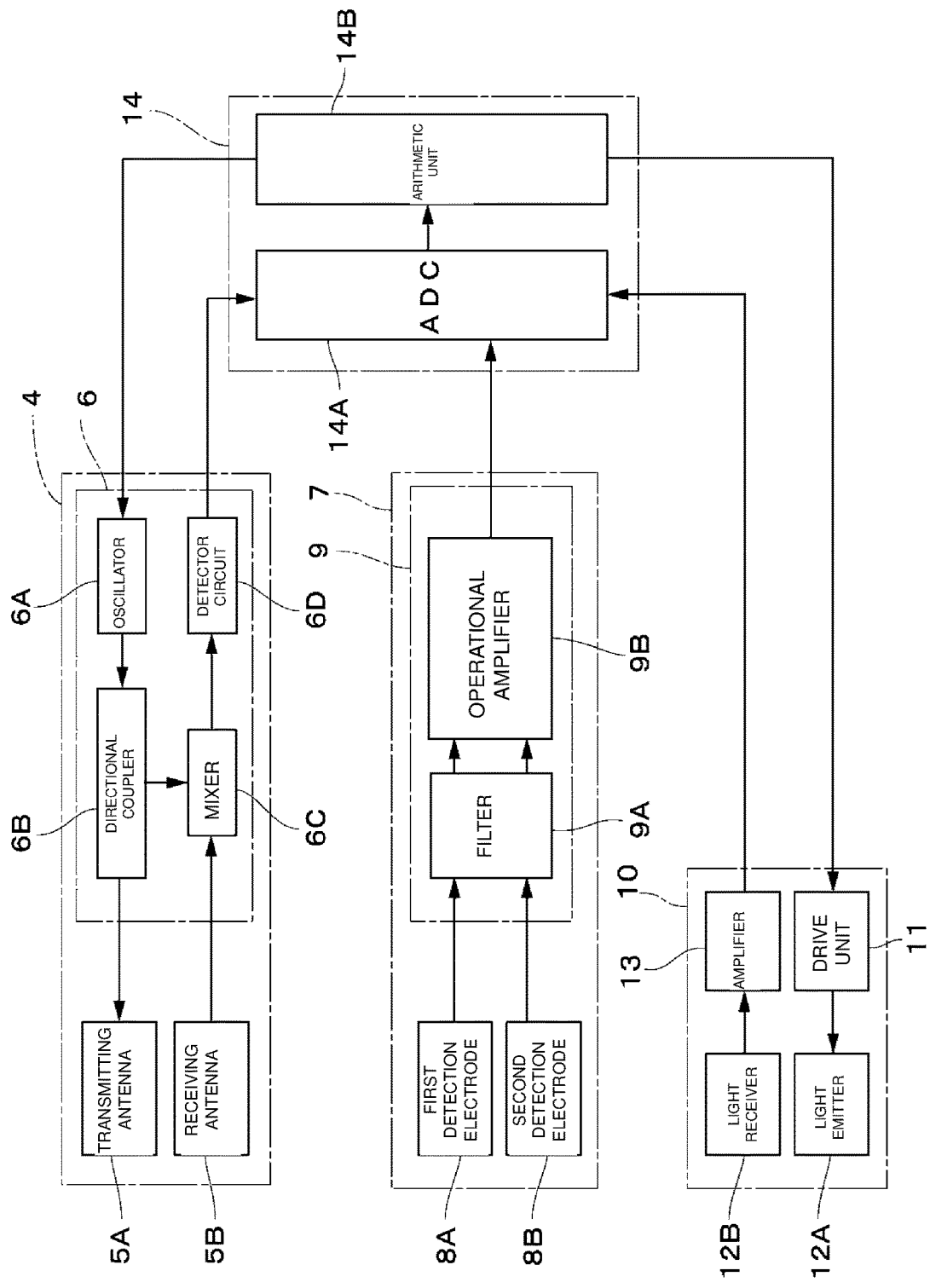
FIG. 4 is a block diagram illustrating the electrical configuration of a heartbeat signal detector, an electrocardiographic signal detector, a pulse wave detector, and a signal processor.

As illustrated in FIG. 4, the heartbeat detecting IC chip 6 includes an oscillator 6A, which generates a transmission signal, a directional coupler 6B, which distributes the transmission signal, a mixer 6C, which mixes a reception signal and the transmission signal, and a detector circuit 6D, which detects a heartbeat signal HBR based on the mixed signal. Accordingly, the heartbeat detecting IC chip 6 outputs the heartbeat signal HBR, indicated by a broken line in FIG. 9, to the signal processor 14 based on the reception signal received by the receiving antenna 5B.

An input side of the oscillator 6A is connected to the signal processor 14, and an output side of the oscillator 6A is connected to the transmitting antenna 5A with the directional coupler 6B interposed therebetween. The oscillator 6A generates a transmission signal including a radio frequency signal such as microwaves or millimeter waves based on a reference signal such as a clock signal output from the signal processor 14, and outputs the transmission signal toward the transmitting antenna 5A. Although the oscillator 6A generates a transmission signal based on a reference signal input from the signal processor 14, the oscillator 6A may generate a transmission signal without using a reference signal.

The directional coupler 6B is provided between the oscillator 6A and the transmitting antenna 5A. An input side of the directional coupler 6B is connected to the oscillator 6A, and an output side of the directional coupler 6B is connected to the transmitting antenna 5A and the mixer 6C. The directional coupler 6B distributes the transmission signal, generated by the oscillator 6A, between the transmitting antenna 5A and the mixer 6C. Accordingly, the directional coupler 6B transmits the transmission signal from the oscillator 6A toward the transmitting antenna 5A and transmits the transmission signal as a sync signal from the oscillator 6A toward the mixer 6C.

The mixer 6C is provided between the receiving antenna 5B and the oscillator 6A. The mixer 6C mixes the sync signal obtained by the oscillator 6A and a reception signal received by the receiving antenna 5B to generate a mixed signal and outputs the mixed signal toward the detector circuit 6D.

An input side of the detector circuit 6D is connected to the mixer 6C, and an output side of the detector circuit 6D is connected to the signal processor 14. The detector circuit 6D includes various wave detector circuits and detects a heartbeat signal HBR from the mixed signal. At this time, the heartbeat signal HBR is, for example, a signal with the Doppler frequency generated when the transmission signal is reflected by the object O. The detector circuit 6D outputs the heartbeat signal HBR toward the signal processor 14.

The electrocardiographic signal detector 7 is provided on the flexible substrate 2 and includes the first and second detection electrodes 8A and 8B, an electrocardiogram detecting IC chip 9, and the like. The electrocardiographic signal detector 7 detects an electrocardiographic signal ECG of the object O. The electrocardiographic signal detector 7 is connectable to the later-described signal processor 14.

The first and second detection electrodes 8A and 8B preferably include a conductive film made of, for example, a conductive metal material or a conductive resin material. The first and second detection electrodes 8A and 8B are provided at two end positions of a diagonal line of the flexible substrate 2 having a rectangular or substantially rectangular shape. In this case, the first and second detection electrodes 8A and 8B are provided at such positions that, while the biometric information sensor 1 is attached to the body surface of the chest or the like of the object O, for example, the index fingers of both hands can be easily brought into contact with portions corresponding to the first and second detection electrodes 8A and 8B. That is, as illustrated in FIG. 1, the first and second detection electrodes 8A and 8B are provided at the upper right-hand corner and the lower left-hand corner of the flexible substrate 2. The first and second detection electrodes 8A and 8B detect analog signals in accordance with the potentials of the body surface (such as the skin of the fingertips) of the object O, and output the analog signals to the electrocardiogram detecting IC chip 9.

The electrocardiogram detecting IC chip 9 is mounted on the flexible substrate 2 using a solder or the like. The electrocardiogram detecting IC chip 9 is driven by power supplied from the battery 16. An input side of the electrocardiogram detecting IC chip 9 is connected to the first and second detection electrodes 8A and 8B, and an output side of the electrocardiogram detecting IC chip 9 is connected to the later-described signal processor 14.

As illustrated in FIG. 4, the electrocardiogram detecting IC chip 9 includes a filter 9A, which removes noise in the analog signals detected by the first and second detection electrodes 8A and 8B, and an operational amplifier 9B, which performs differential amplification of the analog signals detected by the first and second detection electrodes 8A and 8B and outputs an electrocardiographic signal ECG. Accordingly, the electrocardiogram detecting IC chip 9 outputs the electrocardiographic signal ECG, indicated by a solid line in FIG. 9, to the signal processor 14 based on the analog signals detected by the first and second detection electrodes 8A and 8B.

An input side of the filter 9A is connected to the first and second detection electrodes 8A and 8B, and an output side of the filter 9A is connected to the operational amplifier 9B. The filter 9A includes, for example, a low-pass filter and removes unnecessary high frequency components from the analog signals detected by the first and second detection electrodes 8A and 8B.

An input side of the operational amplifier 9B is connected to the first and second detection electrodes 8A and 8B, and an output side of the operational amplifier 9B is connected to the signal processor 14. The operational amplifier 9B defines a differential amplifier circuit that amplifies a potential difference between the analog signals detected by the first and second detection electrodes 8A and 8B. The signal obtained by differential amplification performed by the operational amplifier 9B is output as an electrocardiographic signal ECG including the differentially amplified signal to the signal processor 14. Note that a differential amplifier circuit other than an operational amplifier may be used as long as the differential amplifier circuit amplifies a potential difference between the analog signals detected by the first and second detection electrodes 8A and 8B.

The pulse wave detector 10 is provided on the flexible substrate 2 and is connected to the signal processor 14. The pulse wave detector 10 includes a driver 11, a light emitter 12A, a light receiver 12B, an amplifier 13, and the like, and detects a photoplethysmographic signal PPG defining and functioning as a pulse wave signal of the object O. Although the pulse wave detector 10 detects a photoplethysmographic signal PPG as a pulse wave signal, a pulse wave signal may be detected using, for example, a muscle pumping pulse wave technique, an air pulse wave technique, an ultrasound Doppler technique, or the like. The pulse wave detector 10 may be driven based on power supplied from the battery 16 or may include a battery (not illustrated), separately from the battery 16, as a driving power supply.

An input side of the driver 11 is connected to the signal processor 14, and an output side of the driver 11 is connected to the light emitter 12A. The driver 11 supplies, to the light emitter 12A, a drive current that causes the light emitter 12A to emit light, based on a drive signal such as a pulse signal input from the signal processor 14.

An input side of the light emitter 12A is connected to the driver 11, and the light emitter 12A performs pulsed light emission with a certain pulse period in accordance with a drive current from the driver 11. Accordingly, the light emitter 12A emits light (such as visible light or infrared light) with a certain wavelength to, for example, the body surface of the object O. At this time, the pulse period is set to a sufficiently small value, compared with the period of a photoplethysmographic signal PPG. The light emitter 12A is formed preferably by sealing a light-emitting element such as a light-emitting diode (LED) with transparent resin. Note that the light emitter 12A may be formed using a Vertical Cavity Surface Emitting LASER (VCSEL) or a resonator-type LED as a light-emitting element, for example. The light emitter 12A may perform not only pulsed light emission, but also temporally continuous light emission.

When, for example, the body surface of the chest of the object O reflects light emitted from the light emitter 12A, the light receiver 12B receives this reflected light. An output side of the light receiver 12B is connected to the amplifier 13, and the light receiver 12B outputs a light detection signal in accordance with the reflected light to the amplifier 13. The light receiver 12B is formed preferably by sealing a light-receiving element such as a photodiode (PD) with transparent resin. Note that the light receiver 12B may be formed using, for example, a photo transistor as a light-receiving element. Although the light receiver 12B receives light reflected by the body surface of the object O or the like, the light receiver 12B may receive light that has passed through the body surface of the object O or the like. Furthermore, the light emitter 12A may emit light not only to the chest of the object O, but also to other portions such as a hand, a finger, or an arm, and the light receiver 12B may receive light reflected by or transmitted through these portions.

An input side of the amplifier 13 is connected to the light receiver 12B, and an output side of the amplifier 13 is connected to the signal processor 14. The amplifier 13 performs current-to-voltage conversion of the light detection signal supplied from the light receiver 12B, amplifies the light detection signal that has gone through the current-to-voltage conversion, and outputs the amplified signal as a photoplethysmographic signal PPG, indicated by a dashed-dotted line in FIG. 9, to the signal processor 14.

The signal processor 14 is provided on the flexible substrate 2 and is driven by power supplied from the battery 16. An input side of the signal processor 14 is connected to the heartbeat signal detector 4, the electrocardiographic signal detector 7, the pulse wave detector 10, and the like. An output side of the signal processor 14 is connected to the heartbeat signal detector 4, the pulse wave detector 10, and a later-described TAG IC chip 15.

The signal processor 14 includes, for example, an MCU (Micro Control Unit or Microcontroller), and includes an ADC (Analog Digital Converter) 14A and an arithmetic processor 14B. The signal processor 14 processes signals based on the heartbeat signal HBR, the electrocardiographic signal ECG, and the photoplethysmographic signal PPG detected from the heartbeat signal detector 4, the electrocardiographic signal detector 7, and the pulse wave detector 10. The signal processor 14 controls the operation of the heartbeat signal detector 4, the pulse wave detector 10, and the later-described TAG IC chip 15 in accordance with various programs.

An input side of the ADC 14A is connected to the heartbeat signal detector 4, the electrocardiographic signal detector 7, and the pulse wave detector 10, and an output side of the ADC 14A is connected to the arithmetic processor 14B. The ADC 14A converts the heartbeat signal HBR, the electrocardiographic signal ECG, and the photoplethysmographic signal PPG, which are analog signals input from the heartbeat signal detector 4, the electrocardiographic signal detector 7, and the pulse wave detector 10, to digital signals, and outputs the digital signals to the arithmetic processor 14B. At this time, the ADC 14A performs analog to digital conversion with a sampling period sufficiently shorter than the signal periods of the heartbeat signal HBR, the electrocardiographic signal ECG, and the photoplethysmographic signal PPG. The ADC 14A is commonly used for the heartbeat signal HBR, the electrocardiographic signal ECG, and the photoplethysmographic signal PPG, and sequentially converts these analog signals to digital signals at different time points. Therefore, the heartbeat signal HBR, the electrocardiographic signal ECG, and the photoplethysmographic signal PPG are adjusted such that their signal intensities and amplitudes are within dynamic ranges that are substantially the same.

Figure 7:
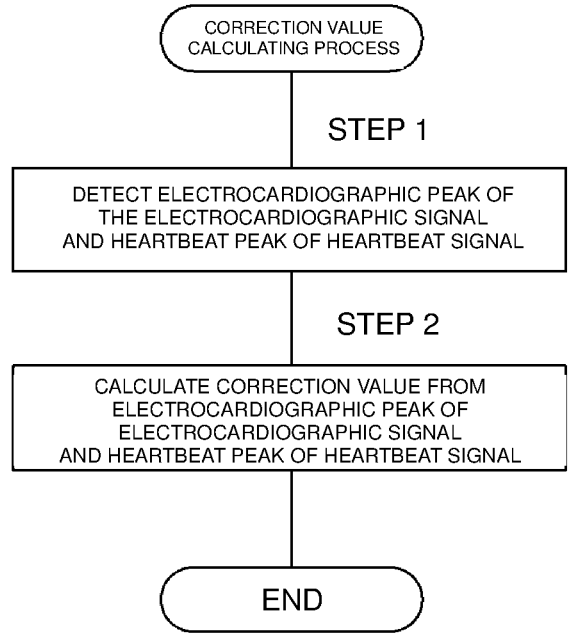
FIG. 7 is a flowchart illustrating a correction value calculating process according to the first preferred embodiment of the present invention.
Figure 8:
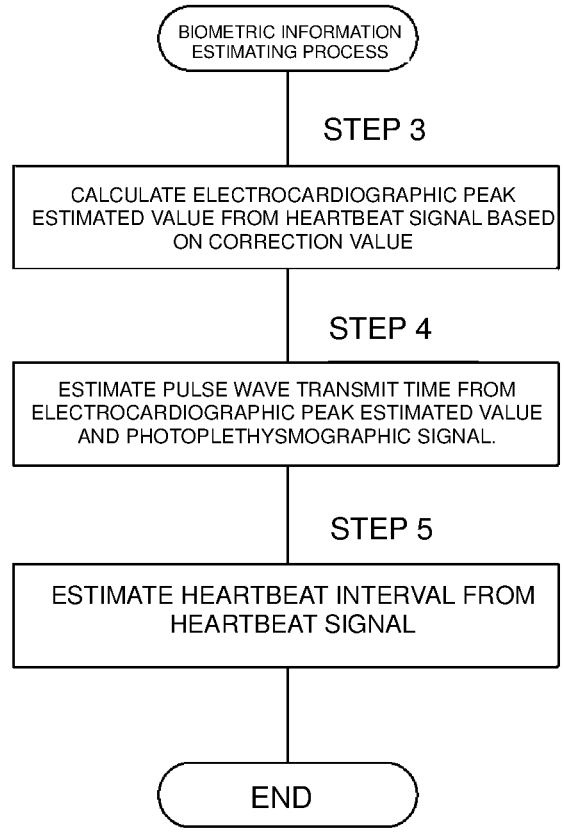
FIG. 8 is a flowchart illustrating a biometric information estimating process according to the first preferred embodiment of the present invention.

The arithmetic processor 14B is configured or programmed to execute a correction value calculating process illustrated in FIG. 7 or a biometric information estimating process illustrated in FIG. 8 based on the heartbeat signal HBR, the electrocardiographic signal ECG, and the photoplethysmographic signal PPG input from the ADC 14A. The arithmetic processor 14B stores a correction value TF calculated by the correction value calculating process, and a pulse wave transmit time PTT and a heartbeat peak time interval R-RI' (heartbeat interval R-RI') calculated by the biometric information estimating process in a memory (not illustrated). To activate the heartbeat signal detector 4, the arithmetic processor 14B outputs a reference signal to the oscillator 6A. To activate the pulse wave detector 10, the arithmetic processor 14B outputs a drive signal to the driver 11.

A selector switch (not illustrated) that selects one of the correction value calculating process and the biometric information estimating process is connected to the arithmetic processor 14B. Therefore, the arithmetic processor 14B executes a process selected by the selector switch.

The TAG IC chip 15 is provided on the flexible substrate 2, includes a memory, a microprocessor, and the like, and is connected to a coil 17. The memory of the TAG IC chip 15 stores, for example, personal information of the object O, and the like. Various items of information stored in the memory are able to be read by an external reading device (not illustrated) using the coil 17.

For example, when the biometric information sensor 1 is put on the reading device, electromagnetic induction occurs in the coil 17, thus supplying power to the TAG IC chip 15. At this time, the TAG IC chip 15 reflects some of the electromagnetic waves generated by the reading device and modulates the information in the memory on the reflected waves. Accordingly, the reading device is able to receive the personal information of the object O based on the reflected waves.

The TAG IC chip 15 is also connected to the signal processor 14. Therefore, the TAG IC chip 15 outputs the information stored in its memory to the reading device, and also outputs the correction value TF, the pulse wave transmit time PTT, and the heartbeat interval R-RI', which are stored in the memory of the signal processor 14, to the reading device. By connecting an output device such as a monitor or a printer to the reading device, the object O is able to check the pulse wave transmit time PTT and the heartbeat interval R-RI' by looking at the output result displayed or printed by the output device.

Note that the correction value TF, the pulse wave transmit time PTT, and the heartbeat interval R-RI' calculated by the arithmetic processor 14B may not necessarily be stored in the memory of the arithmetic processor 14B; instead, these items of information may be stored in the memory of the TAG IC chip 15 and output to the reading device along with the personal information and the like. The TAG IC chip 15 is not limited to a passive chip driven by power supplied from the reading device, and may be an active chip driven by power supplied from the battery 16. The pulse wave transmit time PTT and the heartbeat interval R-RI' may be successively output to an external device, instead of being stored in the memory. In this case, the pulse wave transmit time PTT and the heartbeat interval R-RI' may be output to the outside using the TAG IC chip 15, the coil 17, and the like, or may be output to the outside using a wireless device separate from the TAG IC chip 15, the coil 17, and the like.

The battery 16 supplies power to the heartbeat detecting IC chip 6, the electrocardiogram detecting IC chip 9, the signal processor 14, and the like. The battery 16 is coupled to both ends of the coil 17 and is charged with power supplied from the coil 17. Alternatively, the battery 16 may be charged through a power supply line separate from the coil 17. The battery 16 may be mounted as an exchangeable battery on the flexible substrate 2.

Figure 5:
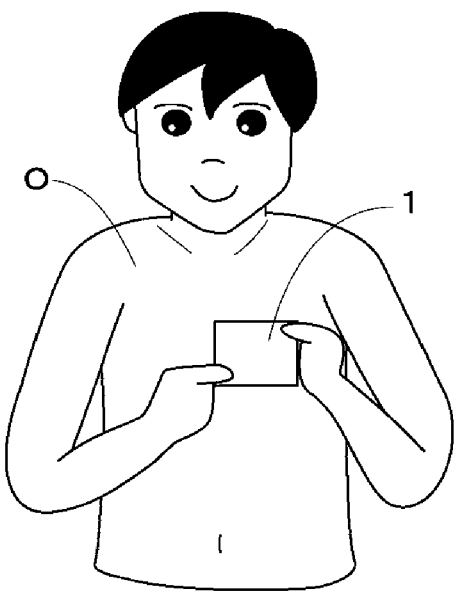
FIG. 5 is a schematic diagram illustrating a state where an object is detecting a heartbeat signal and an electrocardiographic signal using the biometric information sensor.

The biometric information sensor 1 transmits a transmission signal toward the heart of the object O using the transmitting antenna 5A of the heartbeat signal detector 4, and receives reflected waves from the heart as a reception signal using the receiving antenna 5B. Therefore, as illustrated in FIG. 5, the biometric information sensor 1 is attached to the body surface of the object O using the adhesive 3, and is placed near the heart (left chest) of the object O.

Next, the operation of the biometric information sensor 1 according to the present preferred embodiment will be described referring to FIGS. 5 to 9.

At first, referring to FIGS. 5 and 7, a correction value calculating process of detecting a heartbeat signal HBR and an electrocardiographic signal ECG of the object O and calculating a correction value TF will be described.

The object O first selects the correction value calculating process using the selector switch.

Next, as illustrated in FIG. 5, the object O, whose chest's body surface is attached with the biometric information sensor 1, brings fingertips of both hands into contact with the first and second detection electrodes 8A and 8B of the electrocardiographic signal detector 7. When the biometric information sensor 1 is activated in this state, both the heartbeat signal detector 4 and the electrocardiographic signal detector 7 are caused to operate together.

The heartbeat signal detector 4 detects a heartbeat signal HBR in accordance with the heartbeats of the object O. Specifically, the oscillator 6A outputs a transmission signal such as microwaves or millimeter waves to the transmitting antenna 5A. The transmitting antenna 5A emits the transmission signal, input from the oscillator 6A, toward the heart of the object O. The transmission signal reflected by the object O is received as a reception signal by the receiving antenna 5B. At this time, the reception signal is a signal obtained by adding the Doppler frequency based on the heartbeats of the object O to the frequency of the transmission signal.

The reception signal received by the receiving antenna 5B is mixed with the transmission signal by the mixer 6C, and the mixed signal is input to the detector circuit 6D. The detector circuit 6D detects a heartbeat signal HBR in accordance with the Doppler frequency based on the heartbeats from the mixed signal, and outputs the heartbeat signal HBR to the signal processor 14.

In contrast, the electrocardiographic signal detector 7 detects an electrocardiographic signal ECG that varies in accordance with the cardiac activity of the object O. Specifically, the first and second detection electrodes 8A and 8B detect potentials of the index fingers of both hands, and output analog signals in accordance with these potentials to the filter 9A.

The filter 9A removes noise, which includes unnecessary high frequency components, from the analog signals detected by the first and second detection electrodes 8A and 8B, and outputs the noise-removed analog signals to the operational amplifier 9B. The operational amplifier 9B performs differential amplification of the two analog signals input from the filter 9A, and outputs an electrocardiographic signal ECG in accordance with the potential difference between the index fingers of both hands. The operational amplifier 9B outputs the electrocardiographic signal ECG to the signal processor 14.

When the heartbeat signal HBR detected by the heartbeat signal detector 4 and the electrocardiographic signal ECG detected by the electrocardiographic signal detector 7 are input to the signal processor 14, the ADC 14A performs analog to digital conversion of the heartbeat signal HBR and the electrocardiographic signal ECG. Also in this case, the signal processor 14 executes the correction value calculating process illustrated in FIG. 7 using the arithmetic processor 14B.

In the correction value calculating process, in step 1, the peak (maximum value) of the R wave, which is the electrocardiographic peak of the electrocardiographic signal ECG, is detected, and also the heartbeat peak of the heartbeat signal HBR (the maximum value of the heartbeat signal HBR) is detected.

Figure 9:
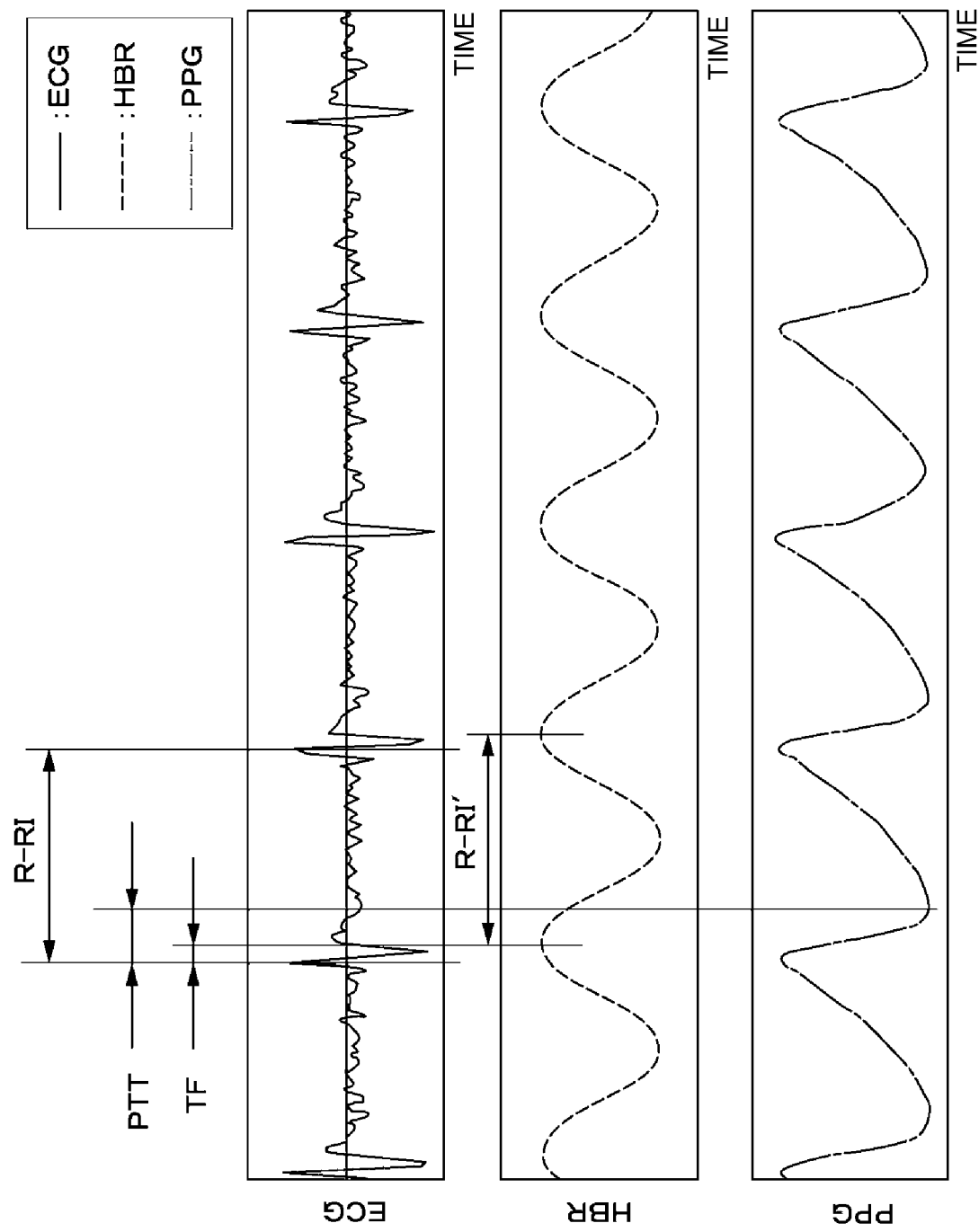
FIG. 9 is a characteristic diagram illustrating a time change of an electrocardiographic signal, a heartbeat signal, and a pulse wave signal.
Figure 10:
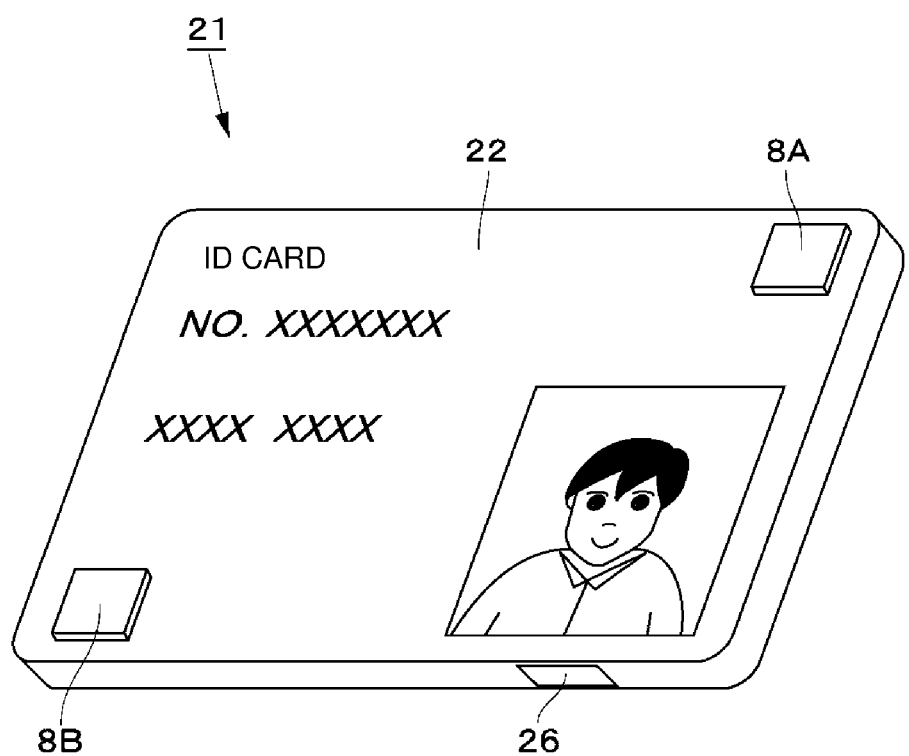
FIG. 10 is a perspective view illustrating a biometric information sensor according to a second preferred embodiment of the present invention.

In the next step 2, a correction value TF is calculated based on the electrocardiographic peak of the electrocardiographic signal ECG and the heartbeat peak of the heartbeat signal HBR. Between the electrocardiographic signal ECG and the heartbeat signal HBR, the phase of the heartbeat signal HBR, which represents the beating of the heart, is delayed, compared with the heartbeat signal HBR, which is an electrical signal. In this case, the correction value TF is calculated by, for example, obtaining the time difference (phase difference) between the electrocardiographic peak of the electrocardiographic signal ECG and the heartbeat peak of the heartbeat signal HBR in the same period, as illustrated in FIG. 9. The calculated correction value TF is stored in the memory of the arithmetic processor 14B.

Alternatively, the correction value TF may be calculated by obtaining the time difference between the electrocardiographic peak and the heartbeat peak in each of a plurality of periods and obtaining the average of these time differences in the plurality of periods.

Alternatively, the correction value TF may be calculated by obtaining the time difference between the electrocardiographic peak of the electrocardiographic signal ECG and the minimum value of the heartbeat signal HBR, or may be calculated by obtaining the time difference between the electrocardiographic peak of the electrocardiographic signal ECG and another portion of the heartbeat signal HBR.

Figure 6:
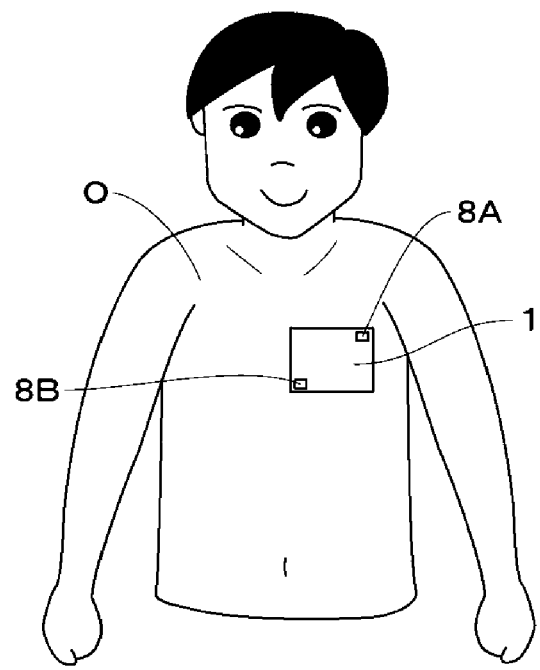
FIG. 6 is a schematic diagram illustrating a state where an object is detecting a heartbeat signal and a pulse wave signal using the biometric information sensor.

Next, referring to FIGS. 6 and 8, a biometric information estimating process of detecting a heartbeat signal HBR and a photoplethysmographic signal PPG of the object O and estimating a pulse wave transmit time PTT and a heartbeat interval R-RI will be described.

The object O first selects the biometric information estimating process using the selector switch. Next, as illustrated in FIG. 6, the object O activates the biometric information sensor 1 while being attached with the biometric information sensor 1 on his/her chest, which then causes both the heartbeat signal detector 4 and the pulse wave detector 10 to operate together.

At this time, the heartbeat signal detector 4 operates in the same manner as in the above-mentioned correction value calculating process, and outputs a heartbeat signal HBR in accordance with the heartbeats of the object O to the signal processor 14. In contrast, the pulse wave detector 10 detects a photoplethysmographic signal PPG that varies in accordance with the cardiac activity of the object O. In this case, the driver 11 supplies, to the light emitter 12A, a drive current that causes the light emitter 12A to emit light, in accordance with a drive signal from the signal processor 14.

The light emitter 12A emits light (such as visible light or infrared light) with a certain wavelength to, for example, the chest of the object O in accordance with the drive current from the driver 11. When the light emitter 12A emits light to the chest of the object O, the light receiver 12B receives light reflected by the chest, converts the light to a light detection signal, and outputs the light detection signal to the amplifier 13. The amplifier 13 performs current-to-voltage conversion of the light detection signal supplied from the light receiver 12B, amplifies the light detection signal that has gone through the current-to-voltage conversion, and outputs the amplified signal as a photoplethysmographic signal PPG to the signal processor 14.

When the photoplethysmographic signal PPG and the heartbeat signal HBR are input to the signal processor 14, the ADC 14A performs analog to digital conversion of the photoplethysmographic signal PPG and the heartbeat signal HBR. Also in this case, the signal processor 14 executes the biometric information estimating process illustrated in FIG. 8 using the arithmetic processor 14B.

In the biometric information estimating process, in step 3, an electrocardiographic peak estimated value is calculated from the heartbeat signal HBR based on the correction value TF obtained in step 2. That is, an electrocardiographic peak estimated value, which is the result of estimating the peak of the R wave of the electrocardiographic signal ECG from the heartbeat signal HBR, is calculated based on the correction value TF obtained from the heartbeat signal HBR detected by the heartbeat signal detector 4 and the electrocardiographic signal ECG detected by the electrocardiographic signal detector 7. Specifically, since the phase of the heartbeat signal HBR is delayed from the electrocardiographic signal ECG, it is considered that an electrocardiographic peak occurs at a time point that is earlier by the correction value TF than the time point of the heartbeat peak of the heartbeat signal HBR. Therefore, an electrocardiographic peak estimated value in accordance with the occurrence time of the electrocardiographic peak is calculated by subtracting the correction value TF from the occurrence time of the heartbeat peak. In this case, step 3 defines and performs the function of an electrocardiographic peak estimator.

In the next step 4, a pulse wave transmit time PTT is estimated from the electrocardiographic peak estimated value obtained in step 3 and the photoplethysmographic signal PPG. That is, a pulse wave transmit time PTT from the peak of the R wave of the electrocardiographic signal ECG to the minimum value of the photoplethysmographic signal PPG is estimated based on the electrocardiographic peak estimated value calculated by the electrocardiographic peak estimator and the photoplethysmographic signal PPG detected by the pulse wave detector 10. Specifically, the minimum value of the photoplethysmographic signal PPG detected by the pulse wave detector 10 is detected, and a time difference is obtained between a time point at which the minimum value of the photoplethysmographic signal PPG occurs and the electrocardiographic peak estimated value, which is the estimated value at a time point at which the electrocardiographic peak occurs. This time difference defines and functions as the estimated value of the pulse wave transmit time PTT. The arithmetic processor 14B stores the estimated pulse wave transmit time PTT in the memory. In this case, step 4 defines and performs the function of a pulse wave transmit time estimator.

In the next step 5, a plurality of heartbeat peaks included in the heartbeat signal HBR are detected, and a time interval R-RI' between adjacent heartbeat peaks is obtained. At this time, since the electrocardiographic signal ECG is synchronous with the heartbeat signal HBR, the heartbeat interval R-RI, which is the time interval between adjacent R waves of the electrocardiographic signal ECG, is considered to be the same or substantially the same value as the time interval R-RI' between the heart beak peaks of the heartbeat signal HBR. Therefore, the heartbeat interval R-RI of the electrocardiographic signal ECG is estimated from the time interval R-RI' of the heartbeat signal HBR. The arithmetic processor 14B stores the estimated heartbeat interval R-RI in the memory.

According to the first preferred embodiment, the biometric information sensor 1 preferably includes the heartbeat signal detector 4 and the signal processor 14. The signal processor 14 is connectable to the electrocardiographic signal detector 7 and the pulse wave detector 10. Therefore, the heartbeat signal HBR, the electrocardiographic signal ECG, and the photoplethysmographic signal PPG, which are the biometric information of the object O, are able to be measured at the same time by the biometric information sensor 1.

The signal processor 14 calculates in advance a correction value TF from the relationship between the heartbeat signal HBR and the electrocardiographic signal ECG, and estimates the R wave of the electrocardiographic signal ECG from the heartbeat signal HBR using the correction value TF. Accordingly, the electrocardiographic peak of the electrocardiographic signal ECG can be indirectly estimated based on the heart beat signal HBR. As a result, once the relationship between the electrocardiographic signal ECG and the heartbeat signal HBR is obtained, the electrocardiographic peak estimated value is able to be calculated by the heartbeat signal detector 4, without using the electrocardiographic signal detector 7.

The signal processor 14 estimates a pulse wave transmit time PTT based on the electrocardiographic peak estimated value and the photoplethysmographic signal PPG. Accordingly, the heartbeat signal detector 4 is able to be used when calculating the pulse wave transmit time PTT. For example, in the case of using the electrocardiographic signal detector 7, it is necessary to attach a plurality of electrodes to portions at different distances from the heart. Compared with this, the object is less constrained in the case of using the heartbeat signal detector 4. As a result, convenience is enhanced, and the pulse wave transmit time PTT is able to be easily estimated.

Since the flexible substrate 2 is preferably included in the biometric information sensor 1, the biometric information sensor 1 is able to be attached in close contact with the body surface of the object O. Accordingly, even when the object O moves, positional displacement of the biometric information sensor 1 is able to be reduced, and biometric information of the object O is able to be accurately detected.

Using the flexible substrate 2 and the adhesive 3, the biometric information sensor 1 is attached to the body surface, near the heart, of the object O. Accordingly, biometric information of the object O is able to be easily detected while enhancing the detection accuracy.

Specifically, using the flexible substrate 2 and the adhesive 3, the heartbeat signal detector 4, the electrocardiographic signal detector 7, and the signal processor 14 are attached to the body surface of the object O. Accordingly, the heartbeat signal HBR and the electrocardiographic signal ECG are able to be detected at the same time using the heartbeat signal detector 4 and the electrocardiographic signal detector 7. A correction value TF used to estimate the electrocardiographic peak from the heartbeat signal HBR is able to be calculated based on the heartbeat signal HBR and the electrocardiographic signal ECG. Furthermore, since the pulse wave detector 10 is provided on the flexible substrate 2, the photoplethysmographic signal PPG of the object O is able to be easily detected while including the biometric information sensor 1 attached to the body surface of the object O.

Since three types of analog signals including the heartbeat signal HBR, the electrocardiographic signal ECG, and the photoplethysmographic signal PPG, which have about the same degree of time change, are input to the signal processor 14, the single ADC 14A is able to convert these analog signals to digital signals. Therefore, the ADC 14A is able to be commonly used for the three types of analog signals, thus reducing the manufacturing cost, compared with the case of providing separate ADCs for the individual signals.

Next, FIGS. 10 to 13 illustrate a second preferred embodiment of the present invention. Features of the second preferred embodiment reside in the point that a biometric information sensor has a card structure, and a pulse wave detector provided separately from a card casing is wired to a signal processor provided in the card casing. In the second preferred embodiment, the same configuration as that of the above-described first preferred embodiment is given the same reference numeral, and a description thereof is omitted.

A biometric information sensor 21 according to the second preferred embodiment includes the heartbeat signal detector 4, the electrocardiographic signal detector 7, the signal processor 14, and the like, like the biometric information sensor according to the first preferred embodiment. However, the biometric information sensor 21 includes the heartbeat signal detector 4, the electrocardiographic signal detector 7, the signal processor 14, and the like in a card casing 22, and the signal processor 14 is wired to a pulse wave detector 23. In this point, the biometric information sensor 21 according to the second preferred embodiment is different from the biometric information sensor 1 according to the first preferred embodiment.

Figure 11:
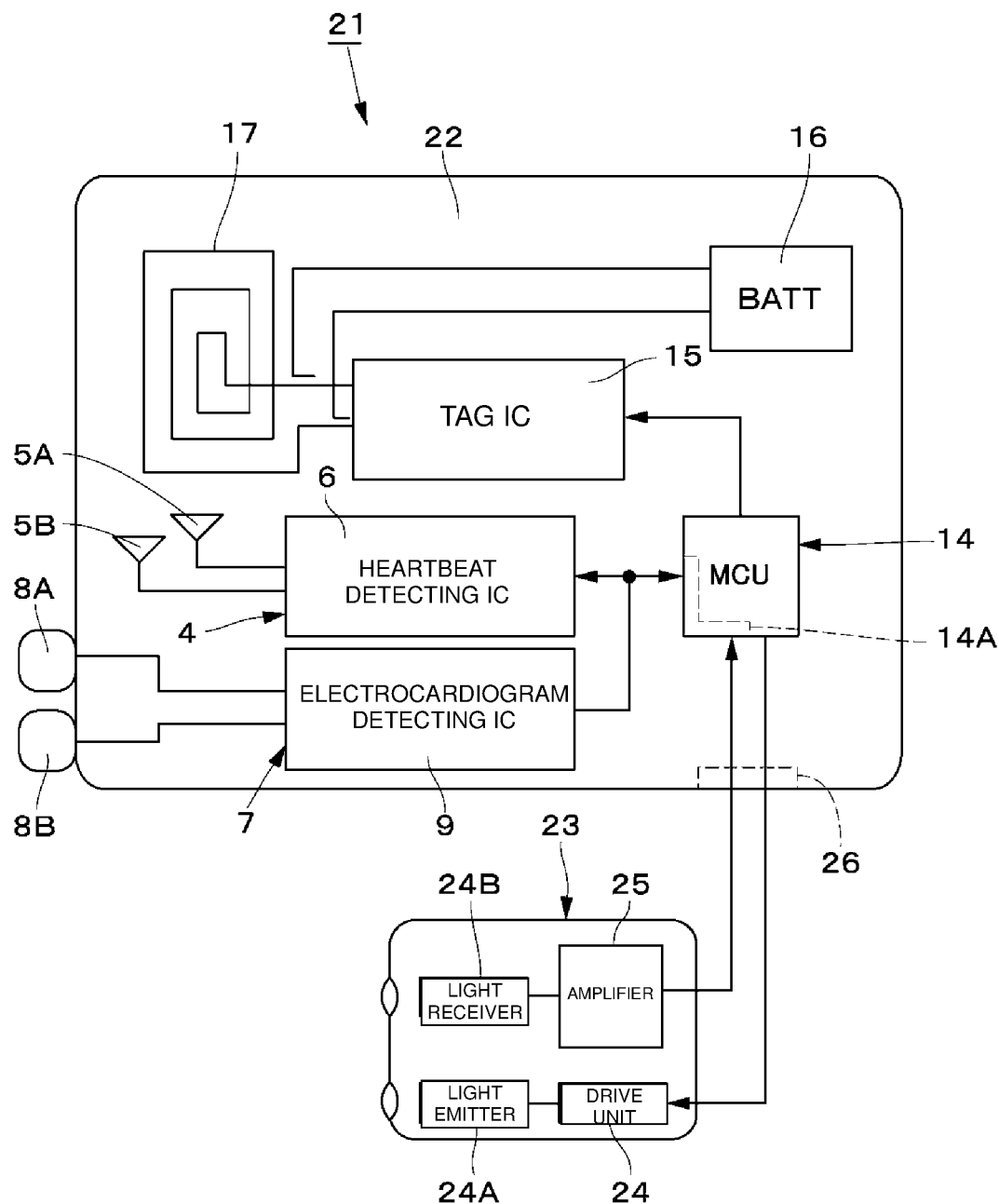
FIG. 11 is a schematic diagram illustrating the internal configuration of the biometric information sensor according to the second preferred embodiment of the present invention.

The card casing 22 defines the covering of the biometric information sensor 21. The card casing 22 includes a thin plate preferably with a rectangular or substantially rectangular shape, which includes a substrate defined by a sheet made of, for example, glass epoxy or the like. As illustrated in FIG. 11, the heartbeat signal detector 4, the electrocardiographic signal detector 7, the signal processor 14, the TAG IC chip 15, the battery 16, the coil 17, and the like are mounted in the card casing 22.

The pulse wave detector 23 is provided separately from the card casing 22, and is connectable to the signal processor 14, provided in the card casing 22, using a connector 26. Like the pulse wave detector 10 of the first preferred embodiment, the pulse wave detector 23 includes a driver 24, a light emitter 24A, a light receiver 24B, an amplifier 25, and the like, and detects a photoplethysmographic signal PPG defining and functioning as a pulse wave signal of the object O.

An input side of the driver 24 is connected to the signal processor 14, and an output side of the driver 24 is connected to the light emitter 24A. The driver 24 supplies, to the light emitter 24A, a drive current that causes the light emitter 24A to emit light, based on a drive signal such as a pulse signal input from the signal processor 14.

An input side of the light emitter 24A is connected to the driver 24, and the light emitter 24A performs pulsed light emission with a certain pulse period in accordance with a drive current from the driver 24. Accordingly, the light emitter 24A emits light with a certain wavelength to, for example, a hand or a finger of the object O. At this time, the pulse period is set to a sufficiently small value, compared with the period of a photoplethysmographic signal PPG.

When, for example, a finger or a hand of the object O reflects light emitted from the light emitter 24A, the light receiver 24B receives this reflected light. An output side of the light receiver 24B is connected to the amplifier 25, and the light receiver 24B outputs a light detection signal in accordance with the reflected light to the amplifier 25.

An input side of the amplifier 25 is connected to the light receiver 24B, and an output side of the amplifier 25 is connected to the signal processor 14. The amplifier 25 performs current-to-voltage conversion of the light detection signal supplied from the light receiver 24B, amplifies the light detection signal that has gone through the current-to-voltage conversion, and outputs the amplified signal as a photoplethysmographic signal PPG to the signal processor 14.

The connector 26 is provided in, for example, a lower portion of the card casing 22, and is connected in a state where a cable of the pulse wave detector 23 is detachable. To measure a photoplethysmographic signal PPG, the cable of the pulse wave detector 23 is connected to the connector 26. The pulse wave detector 23 is wired to the signal processor 14 by using this connector 26. In contrast, the cable of the pulse wave detector is disconnected from the connector 26 when not measuring a photoplethysmographic signal PPG. In this case, when the connector 26 and the pulse wave detector 23 are not connected to each other, the arithmetic processor 14B may execute the correction value calculating process; and, when the connector 26 and the pulse wave detector 23 are connected to each other, the arithmetic processor 14B may execute the biometric information estimating process.

The biometric information sensor 21 transmits a transmission signal toward the heart of the object O using the transmitting antenna 5A of the heartbeat signal detector 4, and receives reflected waves from the heart as a reception signal using the receiving antenna 5B. Therefore, as illustrated in FIGS. 12 and 13, the biometric information sensor 21 is attached to the clothes of the object O using a clip 27 defining and functioning as an attachment member, and is placed near the heart (left chest) of the object O.

Next, the operation of the biometric information sensor 21 according to the present preferred embodiment will be described referring to FIGS. 12 and 13.

The object O first selects the correction value calculating process using the selector switch.

Figure 12:
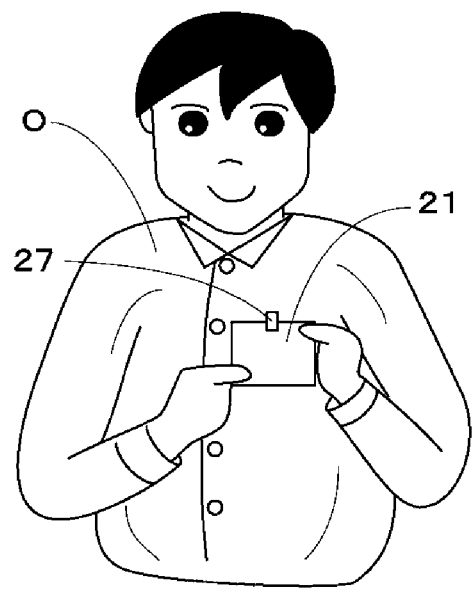
FIG. 12 is a schematic diagram illustrating a state where an object is detecting a heartbeat signal and an electrocardiographic signal using the biometric information sensor according to the second preferred embodiment of the present invention.
Figure 13:
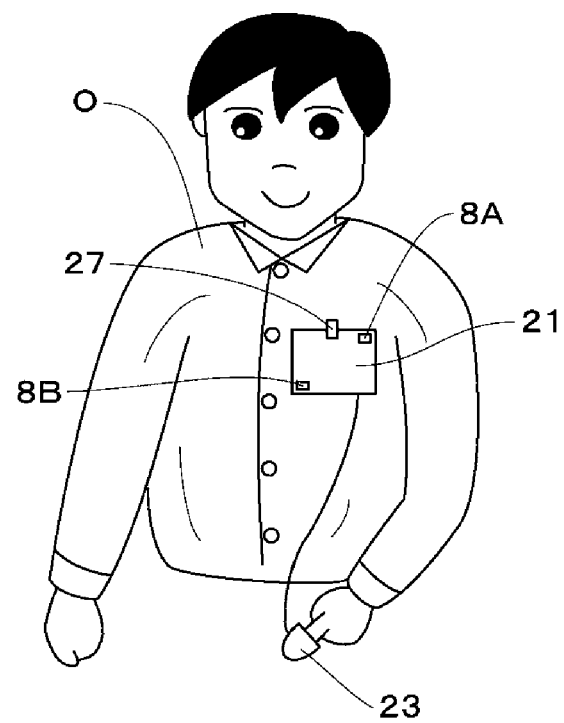
FIG. 13 is a schematic diagram illustrating a state where an object is detecting a heartbeat signal and a pulse wave signal using the biometric information sensor according to the second preferred embodiment of the present invention.

As illustrated in FIG. 12, the object O activates the biometric information sensor 21 while holding the first and second detection electrodes 8A and 8B of the electrocardiographic signal detector 7 in both hands, which then causes both the electrocardiographic signal detector 7 and the heartbeat signal detector 4 to operate together. Accordingly, a heartbeat signal HBR and an electrocardiographic signal ECG of the object O are detected, and a correction value TF is calculated. Since the correction value calculating process is the same as that described in the first preferred embodiment, a description thereof will be omitted.

Next, using FIG. 13, a biometric information estimating process of detecting a heartbeat signal HBR and a photoplethysmographic signal PPG of the object O and estimating a pulse wave transmit time PTT and a heartbeat interval R-RI will be described.

The object O first selects the biometric information estimating process using the selector switch. As illustrated in FIG. 13, the object O activates the biometric information sensor 21 while being attached with the biometric information sensor 21 on his/her finger, which then activates both the heartbeat signal detector 4 and the pulse wave detector 23 together.

At this time, the heartbeat signal detector 4 operates in the same manner as in the above-mentioned correction value calculating process, and outputs a heartbeat signal HBR in accordance with the heartbeats of the object O to the signal processor 14. In contrast, the pulse wave detector 23 detects a photoplethysmographic signal PPG that varies in accordance with the cardiac activity of the object O. In this case, the driver 24 supplies, to the light emitter 24A, a drive current that causes the light emitter 24A to emit light, in accordance with a drive signal from the signal processor 14.

The light emitter 24A emits light with a certain wavelength to, for example, a finger of the object O in accordance with the drive current from the driver 24. When the light emitter 24A emits light to the finger of the object O, the light receiver 24B receives light reflected by the finger, converts the light to a light detection signal, and outputs the light detection signal to the amplifier 25. The amplifier 25 performs current-to-voltage conversion of the light detection signal supplied from the light receiver 24B, amplifies the light detection signal that has gone through the current-to-voltage conversion, and outputs the amplified signal as a photoplethysmographic signal PPG to the signal processor 14.

When the photoplethysmographic signal PPG and the heartbeat signal HBR are input to the signal processor 14, the ADC 14A performs analog to digital conversion of the photoplethysmographic signal PPG and the heartbeat signal HBR, and the arithmetic processor 14B executes the biometric information estimating process. Since the biometric information estimating process is the same as that described in the first preferred embodiment, a description thereof will be omitted.

According to the second preferred embodiment, advantageous effects that are substantially the same as those of the first preferred embodiment are achieved. The biometric information sensor 21 of the second preferred embodiment is configured using the card casing 22. Accordingly, a card biometric information sensor that is small and highly portable enhances convenience and easily detect biometric information of the object O.

Specifically, the heartbeat signal detector 4, the electrocardiographic signal detector 7, and the signal processor 14 are provided in the card casing 22. Accordingly, the heartbeat signal HBR and the electrocardiographic signal ECG are able to be detected at the same time using the heartbeat signal detector 4 and the electrocardiographic signal detector 7 provided in the card casing 22, which enables calculation of the electrocardiographic peak estimated value by using the electrocardiographic peak estimator.

The signal processor 14 includes a pulse wave transmit time estimator that estimates a pulse wave transmit time PTT based on the electrocardiographic peak estimated value and the photoplethysmographic signal PPG. Accordingly, when calculating the pulse wave transmit time PTT, the heartbeat signal detector 4, which performs the measurement without being in contact with the object O, is able to be used. As a result, convenience is be enhanced and the pulse wave transmit time PTT is able to be easily estimated, compared with the case of using the electrocardiographic signal detector 7, which requires the detection electrodes 8A and 8B to be in contact with the object O.

The signal processor 14 is wired to the pulse wave detector 23. Accordingly, the signal processor 14 is able to measure both the heartbeat signal HBR from the heartbeat signal detector 4 and the photoplethysmographic signal PPG from the pulse wave detector 23 without having a time delay between the two signals. Therefore, the pulse wave transmit time PTT is able to be estimated based on the heartbeat signal HBR and the photoplethysmographic signal PPG. In addition to this, connection is able to be certainly established between the signal processor 14 and the pulse wave detector 23, and connection reliability is able to be enhanced.

Figure 14:
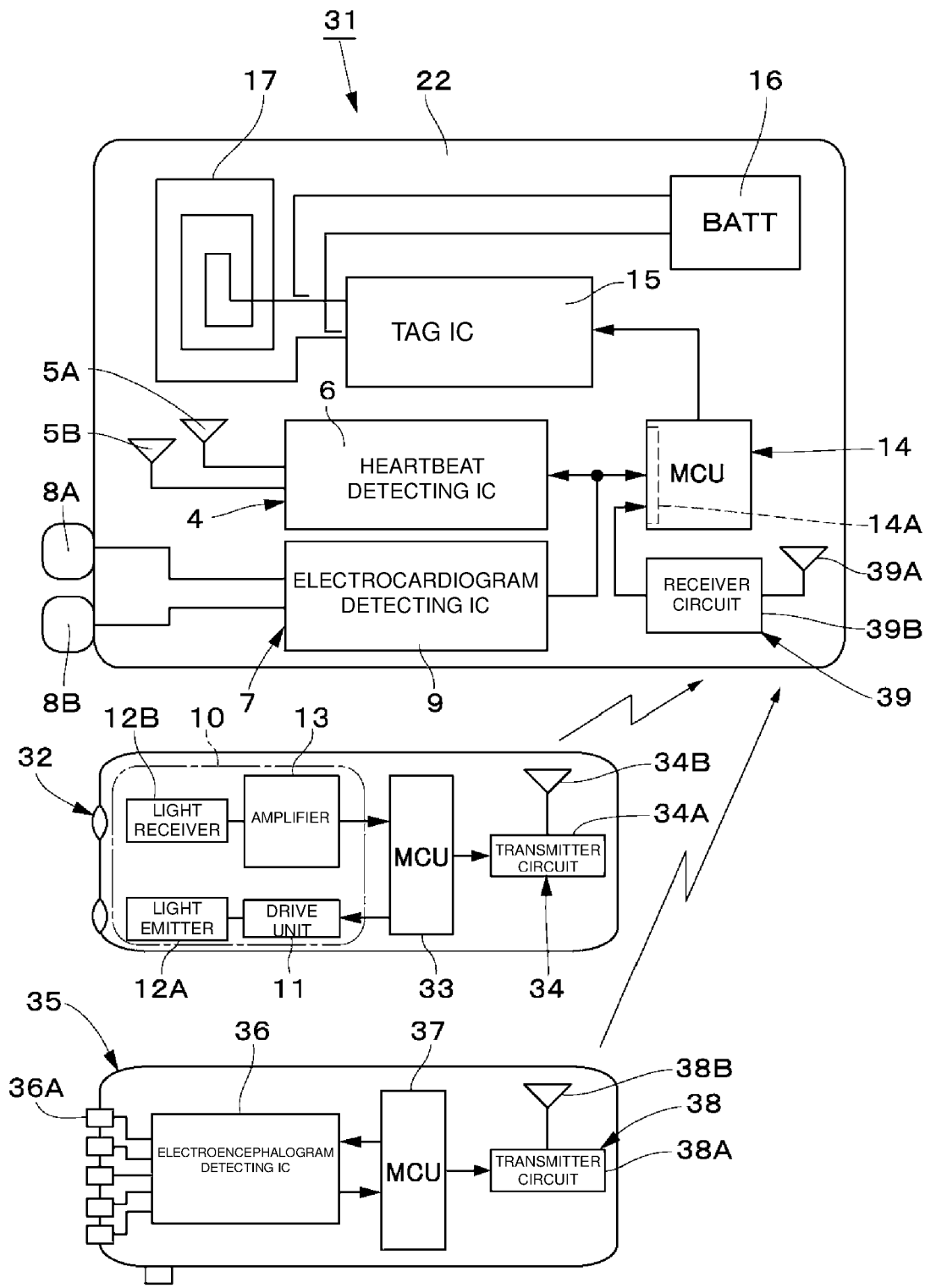
FIG. 14 is a schematic diagram illustrating the internal configuration of a biometric information sensor according to a third preferred embodiment of the present invention.

Next, FIG. 14 illustrates a third preferred embodiment of the present invention. Features of the third preferred embodiment reside in the point that a pulse wave sensor is provided separately from a card casing, and the pulse wave sensor and a signal processor are wirelessly connected. In the third preferred embodiment, the same configuration as that of the above-described first and second preferred embodiments is given the same reference numeral, and a description thereof is omitted.

A biometric information sensor 31 according to the third preferred embodiment includes the card casing 22, the heartbeat signal detector 4, the electrocardiographic signal detector 7, the signal processor 14, and the like, like the biometric information sensor 21 according to the second preferred embodiment. Note that the biometric information sensor 31 includes a pulse wave sensor 32 separately from the card casing 22, and the signal processor 14 and the pulse wave sensor 32 are wirelessly connected using a receiver 39 provided in the card casing 22. In this point, the biometric information sensor 31 according to the third preferred embodiment is different from the biometric information sensors 1 and 21 according to the first and second preferred embodiments.

The pulse wave sensor 32 is provided separately from the card casing 22, and is wirelessly connected to the signal processor 14 provided in the card casing 22 through a transmitter 34 and the receiver 39. The pulse wave sensor 32 includes the pulse wave detector 10, a pulse wave signal processor 33, and the transmitter 34. The pulse wave sensor 32 detects a photoplethysmographic signal PPG defining and functioning as a pulse wave signal of the object O, and transmits the photoplethysmographic signal PPG to the signal processor 14 using the transmitter 34.

An input side of the pulse wave signal processor 33 is connected to the amplifier 13, and an output side of the pulse wave signal processor 33 is connected to the driver 11 and the transmitter 34. The pulse wave signal processor 33 includes an MCU or the like, and outputs a drive signal to drive the light emitter 12A to the driver 11 of the pulse wave detector 10. The pulse wave signal processor 33 outputs the photoplethysmographic signal PPG, detected by the pulse wave detector 10, to the transmitter 34 in order to transmit the photoplethysmographic signal PPG to the signal processor 14.

The transmitter 34 is connected to the pulse wave signal processor 33 and transmits the photoplethysmographic signal PPG, detected by the pulse wave detector 10, to the later-described receiver 39. The transmitter 34 includes a transmitter circuit 34A, which generates a transmission signal, and a transmitting antenna 34B, which outputs the transmission signal.

An input side of the transmitter circuit 34A is connected to the pulse wave signal processor 33, and an output side of the transmitter circuit 34A is connected to the transmitting antenna 34B. The transmitter circuit 34A includes an oscillator (not illustrated) that outputs a carrier wave in a frequency band different from that of a transmission signal or a reception signal of the heartbeat signal detector 4, for example. The transmitter circuit 34A modulates the photoplethysmographic signal PPG, detected by the pulse wave detector 10, on a carrier wave, and outputs a pulse wave transmission signal. The transmitting antenna 34B is connected to the transmitter circuit 34A and includes various antennas such as a patch antenna and a slot antenna. The transmitting antenna 34B transmits the pulse wave transmission signal, generated by the transmitter circuit 34A, toward the receiver 39.

An electroencephalographic (EEG) sensor 35 is provided separately from the card casing 22, and is wirelessly connected to the signal processor 14 provided in the card casing 22 through a transmitter 38 and the receiver 39, which will be described later. The electroencephalographic sensor 35 includes an electroencephalogram detecting IC chip 36, an electroencephalographic signal processor 37, the transmitter 38, and the like. The electroencephalogram detecting IC chip 36 detects an electroencephalographic signal of the object O using electrodes 36A, and inputs the electroencephalographic signal to the electroencephalographic signal processor 37. The electroencephalographic signal processor 37 includes an MCU or the like, and outputs the electroencephalographic signal, input from the electroencephalogram detecting IC chip 36, to the transmitter 38 in order to transmit the electroencephalographic signal to the signal processor 14. The transmitter 38 is preferably configured in substantially the same manner as the transmitter 34 of the pulse wave sensor 32. The transmitter 38 generates an electroencephalographic transmission signal by modulating the electroencephalographic signal on a carrier wave using a transmitter circuit 38A, and transmits the electroencephalographic transmission signal toward the receiver 39 using a transmitting antenna 38B.

The receiver 39 is provided in the card casing 22 and is connected to the signal processor 14. For example, two receivers 39 are provided (only one receiver 39 is illustrated) in accordance with the sensors 32 and 35, which are wirelessly connected to the biometric information sensor 31. Each receiver 39 includes a receiving antenna 39A, which receives a transmission signal, and a receiver circuit 39B, which processes a reception signal. The receiving antenna 39A is connected to the receiver circuit 39B and includes various antennas such as a patch antenna and a slot antenna. An input side of the receiver circuit 39B is connected to the receiving antenna 39A, and an output side of the receiver circuit 39B is connected to the ADC 14A of the signal processor 14.

In the receiver 39 for the pulse wave sensor 32, the receiving antenna 39A receives a pulse wave transmission signal transmitted from the pulse wave sensor 32. The receiver circuit 39B demodulates a photoplethysmographic signal PPG from the pulse wave transmission signal, and outputs the photoplethysmographic signal PPG toward the ADC 14A.

In contrast, in the receiver 39 for the electroencephalographic sensor 35, the receiving antenna 39A receives an electroencephalographic transmission signal transmitted from the electroencephalographic sensor 35. The receiver circuit 39B demodulates an electroencephalographic signal from the electroencephalographic transmission signal, and outputs the electroencephalographic signal toward the ADC 14A.

The photoplethysmographic signal PPG and the electroencephalographic signal output from the receiver circuits 39B are changed by the ADC 14A to digital signals and input to the arithmetic processor 14B of the signal processor 14. Here, because the photoplethysmographic signal PPG and the electroencephalographic signal detected by the sensors 32 and 35 are subjected to modulation and demodulation of a pulse wave transmission signal and an electroencephalographic transmission signal defining and functioning as wireless signals until these signals are input to the arithmetic processor 14B, a delay time occurs due to such signal processing. Therefore, the arithmetic processor 14B according to the third preferred embodiment determines in advance the delay time based on the results of in-advance experiments or the like, and performs correction of a time (phase difference) with respect to the heartbeat signal HBR. Accordingly, even the signal processor 14 according to the third preferred embodiment is able to estimate the pulse wave transmit time PTT, like the signal processor 14 according to the first preferred embodiment.

Even in the third preferred embodiment, advantageous effects that are substantially the same as those of the first preferred embodiment are achieved. In the biometric information sensor 31, the pulse wave sensor 32 is provided separately from the card casing 22, and the pulse wave sensor 32 and the signal processor 14 are wirelessly connected to each other. Accordingly, compared with the case where the pulse wave sensor 32 is wired to the signal processor 14, there is no wiring at the time of measurement, and the wearability of the biometric information sensor 31 for the object O is enhanced. As a result, once the electrocardiographic peak estimated value is calculated from the electrocardiographic signal ECG, the electrocardiographic signal detector 7 is able to be detached from the object O. Therefore, in the case of measuring the pulse wave transmit time PTT, the degree of freedom in movement of the object O is enhanced, and convenience can be enhanced.

Since the signal processor 14 determines in advance a delay time of a signal involved in wireless connection, the photoplethysmographic signal PPG and the electroencephalographic signal from the sensors 32 and 35, which are wirelessly connected, and the heartbeat signal HBR from the heartbeat signal detector 4 and the electrocardiographic signal ECG from the electrocardiographic signal detector 7, which are provided in the card casing 22, are able to be measured together. That is, a signal delay involved in wireless connection is able to be corrected as an analog circuit delay by advancing the phase of the photoplethysmographic signal PPG and the electroencephalographic signal by the delay time. Accordingly, the photoplethysmographic signal PPG and the electroencephalographic signal, and the heartbeat signal HBR and the electrocardiographic signal ECG, is able to be obtained as items of data comparable to each other in the same reference time. As a result, like the first preferred embodiment, the signal processor 14 including an MCU executes a peak time determination process, thus estimating the pulse wave transmit time PTT and the heartbeat interval R-RI.

In the third preferred embodiment, the number (such as two) of receivers 39, provided in the card casing 22, preferably is the number of sensors 32 and 35 which are wirelessly connected. However, the present invention is not limited to this case, and a single receiver 39 may be provided in the card casing 22, and wireless connection may be established with one of the plurality of sensors 32 and 35. Although the plurality of sensors 32 and 35 measure signals of different types, as in the photoplethysmographic signal PPG and the electroencephalographic signal, the sensors 32 and 35 may measure signals of the same type (such as the photoplethysmographic signal PPG) measured in different portions.

Figure 15:
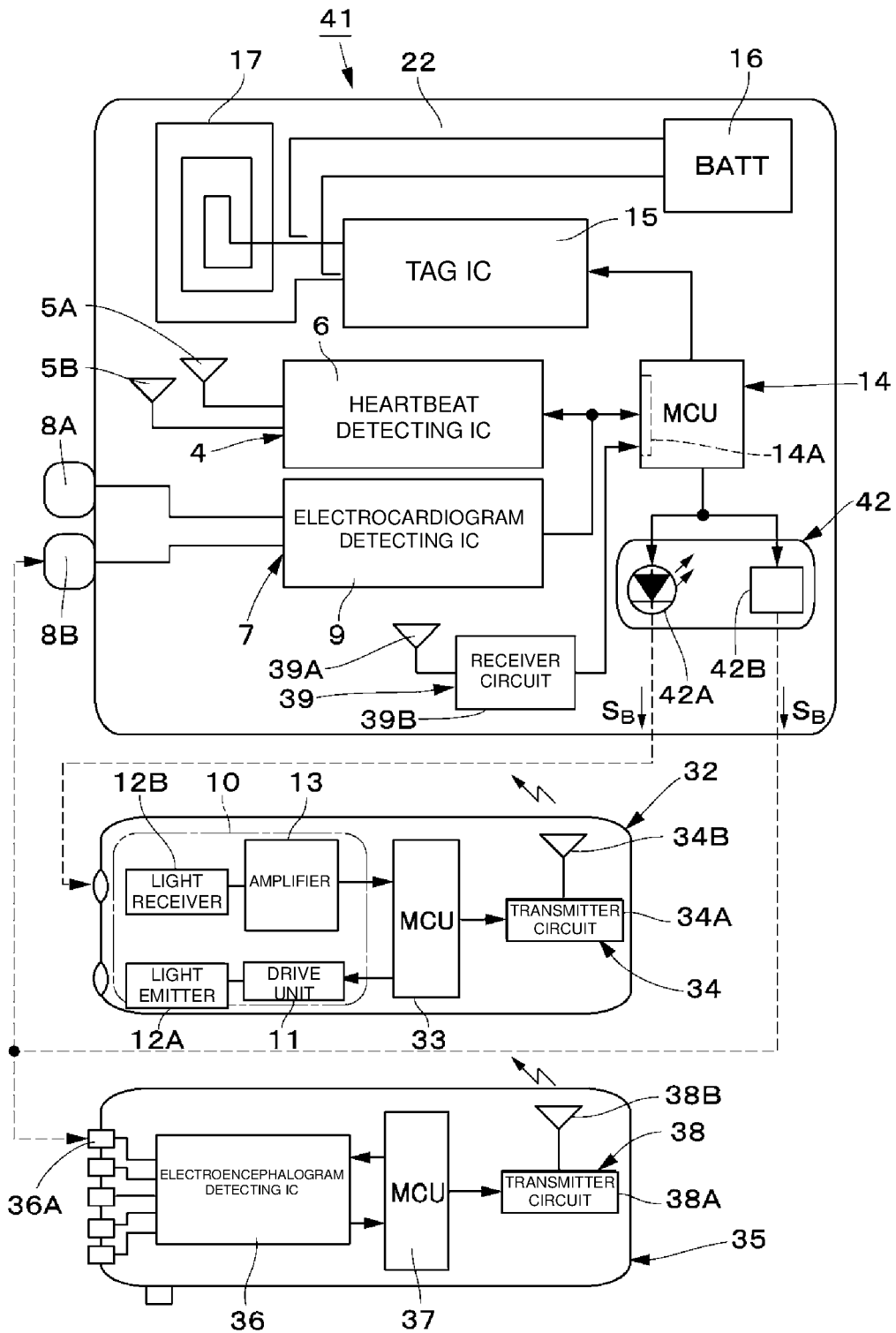
FIG. 15 is a schematic diagram illustrating the internal configuration of a biometric information sensor according to a fourth preferred embodiment of the present invention.
Figure 16:
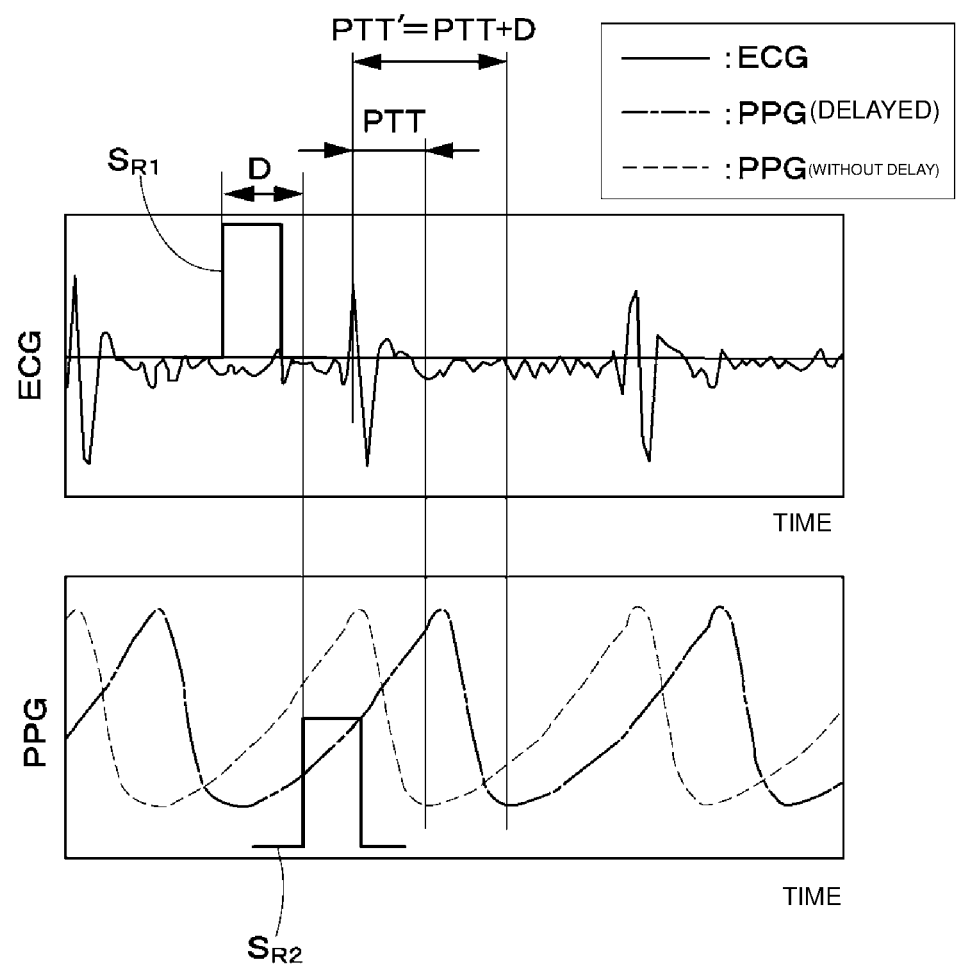
FIG. 16 is a characteristic diagram illustrating a time change of an electrocardiographic signal, a pulse wave signal, and a response signal based on a reference signal according to the fourth preferred embodiment of the present invention.

Next, FIGS. 15 and 16 illustrate a fourth preferred embodiment of the present invention. A feature of the fourth preferred embodiment resides in the point that a reference signal output that outputs a reference signal is provided in a card casing. In the fourth preferred embodiment, the same configuration as that of the above-described first, second, and third preferred embodiments is given the same reference numeral, and a description thereof is omitted.

A biometric information sensor 41 according to the fourth preferred embodiment includes the card casing 22, the heartbeat signal detector 4, the electrocardiographic signal detector 7, the signal processor 14, the pulse wave sensor 32, and the like, like the biometric information sensor 31 according to the third preferred embodiment. Note that the biometric information sensor 41 includes a reference signal output 42 in the card casing 22. In this point, the biometric information sensor 41 according to the fourth preferred embodiment is different from the biometric information sensors 1, 21, and 31 according to the first, second, and third preferred embodiments.

The reference signal output 42 is provided in the card casing 22 and is connected to the signal processor 14. The reference signal output 42 includes an optical signal output 42A and an electrical signal output 42B, which output a reference signal $S_B$. The reference signal output 42 outputs the reference signal $S_B$ to the electrocardiographic signal detector 7, the pulse wave sensor 32, and the electroencephalographic sensor 35 based on an operation command from the signal processor 14. At this time, the reference signal $S_B$ includes a beacon signal that outputs a pulse signal with a certain period greater than or equal to a few tens of ms and less than or equal to a few hundreds of ms.

An input side of the optical signal output 42A is connected to the signal processor 14, and the optical signal output 42A includes a light-emitting element such as a light-emitting diode (LED). The optical signal output 42A converts the reference signal $S_B$ to an optical signal and outputs the optical signal. That is, the optical signal output 42A performs pulsed light emission in accordance with the reference signal $S_B$. The optical signal output 42A outputs the optical signal in accordance with the reference signal $S_B$ toward the light receiver 12B of the pulse wave sensor 32.

An input side of the electrical signal output 42B is connected to the signal processor 14, and an output terminal (not illustrated) made of, for example, a conductive metal is connected to an output side of the electrical signal output 42B. The electrical signal output 42B outputs a voltage signal in accordance with the reference signal $S_B$. The output terminal of the electrical signal output 42B is connected to the second detection electrode 8B of the electrocardiographic signal detector 7 and the electrodes 36A of the electroencephalographic sensor 35 using, for example, connection cables. Accordingly, the electrical signal output 42B outputs the reference signal $S_B$ to the electrocardiographic signal detector 7 and the electroencephalographic sensor 35. Note that it is only necessary for the reference signal $S_B$ to be input to either of the detection electrodes 8A and 8B of the electrocardiographic signal detector 7. The reference signal $S_B$ may be input to the first detection electrode 8A.

The signal processor 14 according to the fourth preferred embodiment measures a delay time D that occurs between the sensors 32 and 35 by using the reference signal output 42, and corrects the photoplethysmographic signal PPG and the electroencephalographic signal based on the measured delay time D. In this point, the fourth preferred embodiment is different from the third preferred embodiment where the delay time D is set in advance.

Next, a delay time measuring process performed by the biometric information sensor 41 according to the fourth preferred embodiment will be described using FIG. 16. Although the case where the delay time D of the pulse wave sensor 32 is measured is described here by way of example, the same applies to the case where a delay time of the electroencephalographic sensor 35 is measured.

At first, the output terminal of the electrical signal output 42B of the reference signal output 42 is connected to the detection electrode 8A or 8B of the electrocardiographic signal detector 7. A light-emitting portion of the optical signal output 42A of the reference signal output 42 is directed facing the light receiver 12B of the pulse wave sensor 32.

In this state, for example, when the delay time measuring process is selected by an initial setting switch (not illustrated), the electrical signal output 42B of the reference signal output 42 outputs a voltage signal in accordance with the reference signal $S_B$, and the optical signal output 42A of the reference signal output 42 outputs an optical signal in accordance with the reference signal $S_B$. Accordingly, the reference signal $S_B$ is output to each of the electrocardiographic signal detector 7 and the pulse wave sensor 32.

At this time, since a potential difference occurs between the first and second detection electrodes 8A and 8B based on the reference signal $S_B$, the electrocardiographic signal detector 7 generates a response signal $S_{R1}$ based on the potential difference. The response signal $S_{R1}$ is input to the signal processor 14. The pulse wave sensor 32 performs photoelectric conversion of the optical signal based on the reference signal $S_B$ to generate a response signal $S_{R2}$, and transmits the response signal $S_{R2}$ toward the receiver 39 using the transmitter 34. The response signal $S_{R2}$ is input to the signal processor 14 through the receiver 39.

The signal processor 14 measures a delay time D that occurs relative to the pulse wave sensor 32 based on the response signals $S_{R1}$ and $S_{R2}$. For example, like the second preferred embodiment, when the pulse wave detector 10 is wired to the signal processor 14, the photoplethysmographic signal PPG is input without delay relative to the electrocardiographic signal ECG, as indicated by a broken line in FIG. 16. In contrast, in the fourth preferred embodiment, since the pulse wave sensor 32 is connected wirelessly to the signal processor 14, the photoplethysmographic signal PPG is delayed relative to the electrocardiographic signal ECG, as indicated by a dashed-dotted line in FIG. 16, and a delay time D occurs. At this time, the delay time D also occurs between the response signal $S_{R1}$ obtained by the electrocardiographic signal detector 7 and the response signal $S_{R2}$ obtained by the pulse wave sensor 32. Thus, the signal processor 14 measures the delay time D and stores the delay time D in a memory (not illustrated).

At this time, since the heartbeat signal detector 4 and the electrocardiographic signal detector 7 are both directly connected to the signal processor 14, no delay occurs between the heartbeat signal HBR and the electrocardiographic signal ECG. Therefore, the same delay time D as that between the electrocardiographic signal ECG and the photoplethysmographic signal PPG occurs between the heartbeat signal HBR and the photoplethysmographic signal PPG. To estimate the pulse wave transmit time PTT, the signal processor 14 corrects a time interval PTT' between the electrocardiographic peak estimated value and the minimum value of the photoplethysmographic signal PPG using the delay time D.

Specifically, when the photoplethysmographic signal PPG is delayed by the delay time D relative to the response signal $S_{R1}$ of the electrocardiographic signal ECG, the time interval PTT' between the electrocardiographic peak estimated value and the minimum value of the photoplethysmographic signal PPG, which is delayed, becomes a time obtained by adding the delay time D to the pulse wave transmit time PT (PTT'=PTT+D). By subtracting the delay time D from the time interval PTT', which is between the electrocardiographic peak estimated value based on the heartbeat signal HBR and the minimum value of the photoplethysmographic signal PPG, the signal processor 14 estimates the pulse wave transmit time PTT between the electrocardiographic peak estimated value and the minimum value of the undelayed photoplethysmographic signal PPG.

Even in the fourth preferred embodiment, advantageous effects that are substantially the same as those of the first preferred embodiment are achieved. Since the biometric information sensor 41 includes the reference signal output 42 in the card casing 22, the signal processor 14 is able to measure the delay time D relative to the pulse wave sensor 32 based on the reference signal $S_B$. Therefore, even when the delay time D is different between the sensors 32 and 35, which are wirelessly connected, the delay time D at that time is able to be measured and corrected, and the pulse wave transmit time PTT is able to be estimated based on the measured delay time D. Accordingly, even when a signal transmission delay occurs between the pulse wave sensor 32 and the signal processor 14, the signal processor 14 is able to estimate the accurate pulse wave transmit time PTT by taking the signal delay into consideration.

In the above-described first preferred embodiment, the detector circuit 6D of the heartbeat signal detector 4 detects the Doppler frequency from the reception signal and calculates the heartbeat signal HBR of the object O. However, the present invention is not limited to this configuration, and the detector circuit may detect a phase difference or an amplitude difference between the transmission signal and the reception signal, and may calculate the heartbeat signal HBR of the object O. The same applies to the second, third, and fourth preferred embodiments.

In the above-described first preferred embodiment, the case where the first and second detection electrodes 8A and 8B of the electrocardiographic signal detector 7 are preferably provided in the upper right-hand corner and the lower left-hand corner of the flexible substrate 2 has been described by way of example. However, the present invention is not limited to this case, and the number or the arrangement positions of detection electrodes may be appropriately set in accordance with the portions of the object O that are brought into contact with the detection electrodes.

In the above-described first preferred embodiment, the electrocardiographic signal detector 7 and the pulse wave detector 10 are preferably provided on the flexible substrate 2. However, the present invention is not limited to this configuration, and, for example, the electrocardiographic signal detector and the pulse wave detector may be provided separately from the flexible substrate, and the electrocardiographic detector and the pulse wave detector may be wired or wirelessly connected to the signal processor. That is, the second, third, and fourth preferred embodiments may be combined with the first preferred embodiment.

In the above-described first preferred embodiment, the portions of the object O that preferably are brought into contact with the first and second detection electrodes 8A and 8B are the index fingers. However, the present invention is not limited to this configuration, and the portions brought into contact with the detection electrodes may be the thumbs, the middle fingers, or the palms. The same applies to the second, third, and fourth preferred embodiments.

In the above-described first preferred embodiment, the single light emitter 12A is preferably used in the pulse wave detector 10. However, the present invention is not limited to this configuration, and, for example, a plurality of light emitters that emit irradiation light in different wavelength ranges may be provided. The same applies to the second, third, and fourth preferred embodiments.

In the above-described first preferred embodiment, the deformable flexible substrate 2 is preferably used in the biometric information sensor 1. However, the present invention is not limited to this configuration, and, for example, the biometric information sensor may use an undeformable substrate.

In the above-described second preferred embodiment, the case where the first and second detection electrodes 8A and 8B of the electrocardiographic signal detector 7 are preferably provided in the upper right-hand corner and the lower left-hand corner of the card casing 22 has been described by way of example. However, the present invention is not limited to this case, and the number or the arrangement positions of detection electrodes may be appropriately set in accordance with the portions of the object O that are brought into contact with the detection electrodes. Detection electrodes may be provided at the tip of cables connected to the card casing (electrocardiogram detecting IC chip). The same applies to the third and fourth preferred embodiments.

In the above-described second preferred embodiment, the electrocardiographic signal detector 7 is preferably provided in the card casing 22. However, the present invention is not limited to this configuration, and, like the pulse wave detector, the electrocardiographic detector may be provided separately from the card casing, and the electrocardiographic detector may be wired or wirelessly connected to the signal processor. The same applies to the third and fourth preferred embodiments.

In the above-described third preferred embodiment, the pulse wave sensor 32 and the electroencephalographic sensor 35 are preferably provided separately from the card casing 22, and the pulse wave sensor 32, the electroencephalographic sensor 35, and the signal processor 14 are wirelessly connected through the receiver 39. However, the present invention is not limited to this configuration, and, for example, a temperature sensor may be provided separately from the card casing 22, and the temperature sensor and the signal processor 14 may be wirelessly connected by near-field communication (NFC) using the coil 17. Accordingly, in addition to the photoplethysmographic signal PPG and the electroencephalographic signal, temperature information such as the temperature of the object O is able to be transmitted to the signal processor. Likewise, the pulse wave sensor 32 and the electroencephalographic sensor 35 may be wirelessly connected by NFC using the coil 17. These configurations are similarly applicable to the fourth preferred embodiment.

In the above-described fourth preferred embodiment, the signal processor 14 preferably measures the delay time D based on the response signal $S_{R1}$ obtained by the electrocardiographic signal detector 7 and the response signal $S_{R2}$ obtained by the pulse wave sensor 32. However, the present invention is not limited to this configuration, and, for example, the signal processor may measure the delay time based on a time at which the reference signal is output from the reference signal output and the response signal obtained by the pulse wave sensor.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A biometric information sensor comprising:
   a heartbeat signal detector that detects a heartbeat signal of an object; and
   a signal processor that processes the heartbeat signal; wherein
   the signal processor is connectable to an electrocardiographic signal detector that detects an electrocardiographic signal of the object and a pulse wave detector that detects a pulse wave signal of the object;

the signal processor includes:
- an electrocardiographic peak estimator that calculates an electrocardiographic peak estimated value by estimating an R wave of the electrocardiographic signal from the heartbeat signal based on the heartbeat signal detected by the heartbeat signal detector and the electrocardiographic signal detected by the electrocardiographic signal detector; and
- a pulse wave transmit time estimator that estimates a pulse wave transmit time from the R wave of the electrocardiographic signal to a minimum value of the pulse wave signal based on the electrocardiographic peak estimated value calculated by the electrocardiographic peak estimator and the pulse wave signal detected by the pulse wave detector;

the biometric information sensor includes a memory that stores the electrocardiographic peak estimated value and the pulse wave transmit time; and the heartbeat signal is detected using a Doppler frequency based on heartbeats of the object.

2. The biometric information sensor according to claim 1, further comprising a flexible substrate and an adhesive, wherein:
the heartbeat signal detector and the signal processor are provided on the flexible substrate; and
the adhesive is capable of being attached to a body surface of the object and is provided on the flexible substrate.

3. The biometric information sensor according to claim 2, wherein the electrocardiographic signal detector and the pulse wave detector are provided on the flexible substrate.

4. The biometric information sensor according to claim 2, wherein the adhesive includes a light transmission portion at a center or an approximate center thereof.

5. The biometric information sensor according to claim 2, wherein the heartbeat signal detector includes a transmitting antenna, a receiving antenna, and a heartbeat detecting IC chip.

6. The biometric information sensor according to claim 5, wherein the heartbeat detecting IC chip includes an oscillator, a directional coupler, a mixer and a detector circuit.

7. The biometric information sensor according to claim 2, further comprising first and second detection electrodes mounted at two ends of a diagonal line on a surface of the flexible substrate.

8. The biometric information sensor according to claim 2, further comprising an electrocardiogram detecting IC chip mounted on the substrate.

9. The biometric information sensor according to claim 8, wherein the electrocardiogram detecting IC chip includes a filter and an operational amplifier.

10. The biometric information sensor according to claim 1, wherein the heartbeat signal detector and the signal processor are provided in a card casing.

11. The biometric information sensor according to claim 10, wherein the electrocardiographic signal detector is provided in the card casing.

12. The biometric information sensor according to claim 1, wherein the signal processor is wired to the pulse wave detector.

13. The biometric information sensor according to claim 1, further comprising a pulse wave sensor including the pulse wave detector and a transmitter that transmits the pulse wave signal to the signal processor; wherein
the pulse wave sensor is wirelessly connected to the signal processor through a receiver that is connected to the signal processor and that receives the pulse wave signal and the transmitter.

14. The biometric information sensor according to claim 13, wherein:
a reference signal output that outputs a reference signal is connected to the signal processor;
the receiver receives a response signal based on the reference signal from the pulse wave sensor; and
the signal processor corrects a signal delay relative to the pulse wave sensor based on the response signal.

15. The biometric information sensor according to claim 13, wherein the biometric information sensor has a card structure including a card casing and the pulse wave sensor is separate from the card casing.

16. The biometric information sensor according to claim 1, wherein the pulse wave detector includes a driver, a light emitter, a light receiver, and an amplifier.

17. The biometric information sensor according to claim 1, wherein the pulse wave signal is a photoplethysmographic signal.

18. The biometric information sensor according to claim 1, wherein the signal processor includes a microcontroller, an analog digital converter, and an arithmetic processor.

19. The biometric information sensor according to claim 18, wherein the arithmetic processor is configured or programmed to perform at least one of a correction value calculating process and a biometric information estimating process.

20. The biometric information sensor according to claim 1, wherein the biometric information sensor has a card structure including a card casing and the pulse wave detector is separate from the card casing.

* * * * *